(12) United States Patent
Kondou et al.

(10) Patent No.: US 9,227,190 B2
(45) Date of Patent: Jan. 5, 2016

(54) SAMPLE MEASURING APPARATUS, REAGENT INFORMATION DISPLAYING METHOD AND COMPUTER PROGRAM PRODUCT

(75) Inventors: Keitarou Kondou, Kobe (JP); Naohiko Matsuo, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 225 days.

(21) Appl. No.: 12/607,656

(22) Filed: Oct. 28, 2009

(65) Prior Publication Data

US 2010/0114501 A1 May 6, 2010

(30) Foreign Application Priority Data

Oct. 31, 2008 (JP) .................. 2008-281470

(51) Int. Cl.
G01N 31/00 (2006.01)
B01L 9/00 (2006.01)
B01L 3/00 (2006.01)
B01L 9/06 (2006.01)
G01N 35/00 (2006.01)

(52) U.S. Cl.
CPC . B01L 9/00 (2013.01); B01L 3/527 (2013.01); B01L 9/06 (2013.01); B01L 2200/143 (2013.01); B01L 2300/027 (2013.01); B01L 2300/0841 (2013.01); G01N 2035/00673 (2013.01); G01N 2035/00891 (2013.01)

(58) Field of Classification Search
CPC .......... G01N 2035/00891; G01N 2035/00673; B01L 3/527
USPC .................... 702/22; 715/215, 823
See application file for complete search history.

(56) References Cited

U.S. PATENT DOCUMENTS

| | | | | |
|---|---|---|---|---|
| 6,090,630 A | * | 7/2000 | Koakutsu et al. | 436/50 |
| 7,062,721 B2 | * | 6/2006 | Jin | 715/843 |
| 2002/0031837 A1 | * | 3/2002 | Matsubara et al. | 436/180 |
| 2006/0059414 A1 | * | 3/2006 | Cory et al. | 715/500 |
| 2008/0063570 A1 | * | 3/2008 | Fujino et al. | 422/99 |

OTHER PUBLICATIONS

Tabbed browsing, http://www.webopedia.com/TERM/T/tabbed_browsing.html (available online Aug. 21, 2008).*

* cited by examiner

Primary Examiner — Timothy H Hwang
(74) Attorney, Agent, or Firm — Sughrue Mion, PLLC

(57) ABSTRACT

The present invention is to present a sample measuring apparatus, comprising: a reagent holder for holding plural kinds of reagents; a measurement unit for measuring a measurement sample, prepared from a sample and plural kinds of reagents held by the reagent holder, for a predetermined measurement item; a display; and a display controller for controlling the display so as to display a screen including a predetermined display area showing a measurable number of times indicating how many times the measuring unit is able to perform a measurement for the predetermined measurement item by using the plural kinds of reagents held by the reagent holder.

23 Claims, 29 Drawing Sheets

FIG. 12

| ITEM | NUMBER OF TESTS | 10  20  30  40 | |
|---|---|---|---|
| PT | 14 | ▨▨ | LIGHT BLUE |
| ATIII | 26 | ▨▨▨▨ | LIGHT BLUE / GRAY |
| Fbg | 5 | ▨ | YELLOW |
| TTO | ? | ? | GRAY |
| Hpt | 0 | | |
| DD | - | | |
| | | | |
| | | | |
| | | | |
| Clean I | 112 | ▨▨▨▨▨▨▨ | |

HOLDER No. (430a) MEASUREABLE NUMBER OF TESTS (430b) — 430

431 — REPLACED

| HOLDER No. | | MEASUREABLE NUMBER OF TESTS |

| ITEM | LOT NUMBER | NUMBER OF TESTS |
|---|---|---|
| PT | 001-0009 | 3 |
|  | 001-0011 | 4 |
|  | 001-0013 | 7 |
| ATIII | 002-0007 | 6 |
|  | 002-0014 | 8 |
|  | 002-0019 | 12 |
| Fbg | 001-0010 | 1 |
|  | 001-0012 | 2 |
|  | 001-0014 | 2 |
| TTO | 002-0008 | ? |
|  | 002-0015 | ? |
|  | 002-0020 | ? |
| Hpt | 001-0015 | 0 |
|  | 001-0017 | 0 |
|  | 001-0019 | 0 |
| DD | 002-0009 | - |
|  | 002-0016 | - |
|  | 002-0021 | - |

| Clean I | 112 | |

431 — REPLACED

| MEASUREMENT ITEM | REAGENT NAME | MEASUREABLE NUMBER OF TIMES |
|---|---|---|
| PT | ○× | 14 |
| APTT | ×○ | - |
|  | △○ |  |
| Fbg | ×× | 5 |
|  | △△ |  |
|  | ○○ |  |
| ATⅢ | △× | 26 |
|  | ×△ |  |
|  | △△ |  |
|  | ○○ |  |
| ⋮ | ⋮ | ⋮ |

| HOLDER NUMBER | REAGENT NAME | ... | USABLE AMOUNT (REMAINING AMOUNT) | REMAINING NUMBER OF TESTS | SET DATE | SET TIME |
|---|---|---|---|---|---|---|
| A1-1 | ○× | ... | 1.2ml | 6 | 2008/10/10 | 12:00 |
| A1-2 | ○△ | ... | - | - | 2008/10/9 | 10:00 |
| ⋮ | ⋮ | ⋮ | ⋮ | ⋮ | ⋮ | ⋮ |

US 9,227,190 B2

SAMPLE MEASURING APPARATUS, REAGENT INFORMATION DISPLAYING METHOD AND COMPUTER PROGRAM PRODUCT

FIELD OF THE INVENTION

The present invention relates to a sample measuring apparatus, a reagent information displaying method in a sample measuring apparatus, and a computer program, and in particular, to a sample measuring apparatus for measuring a sample on a predetermined measurement item using a plural kinds of reagents, a reagent information displaying method in a sample measuring apparatus, and a computer program product.

BACKGROUND

Conventionally, for example, U.S. Patent Publication No. 2008/0063570 discloses a sample analyzer for performing a measurement of a sample on a predetermined measurement item using plural kinds of reagents.

The sample analyzer described in U.S. Patent Publication No. 2008/0063570 is configured to perform measurement of a blood sample on a predetermined measurement item using plural kinds of reagents. Plural kinds of reagents are arranged in a reagent arrangement unit in the sample analyzer. The sample analyzer of U.S. Patent Publication No. 2008/0063570 is also configured to display, on a display, a reagent management screen including a reagent arrangement display area indicating an arrangement position of a reagent in the reagent arrangement unit and a detailed information display area for displaying the reagent information of the reagent. The reagent arrangement display area displays a reagent mark corresponding to each reagent in a specifiable manner, and the detailed information display area displays detailed information (e.g., reagent remaining amount, remaining number of tests (remaining number of times the reagent can be used for the measurement of the measurement item using the reagent) and the like) of the reagent corresponding to the specified reagent mark.

In a sample analyzer for performing an analysis of a sample, it is desired to grasp, before starting a measurement, how many more times a measurement item of a measurement target can be measured using reagents arranged in a reagent arrangement unit so as not to recognize lack of remaining amount of a reagent during the measurement operation by the analyzer.

However, in the sample analyzer described in U.S. Patent Publication No. 2008/0063570, the remaining number of tests can only be displayed for every specified reagent. Thus, for example, in order to grasp how many measurements can be performed on the measurement item "Fbg (fibrinogen)", the user needs to specify the kind of a plural of reagents used for the measurement item of the "Fbg", find the reagent mark corresponding to the reagent of the specified kind from a plural of reagent marks displayed on the display screen, specify the reagent mark corresponding to the respective reagent, and display the remaining number of tests of each reagent on the display screen to check the least remaining number of tests. This imposes a burden on the user.

SUMMARY

A first aspect of the present invention is a sample measuring apparatus, comprising:

a reagent holder for holding plural kinds of reagents;
a measurement unit for measuring a measurement sample, prepared from a sample and plural kinds of reagents held by the reagent holder, for a predetermined measurement item;
a display; and
a display controller for controlling the display so as to display a screen including a predetermined display area showing a measurable number of times indicating how many times the measuring unit is able to perform a measurement for the predetermined measurement item by using the plural kinds of reagents held by the reagent holder.

A second aspect of the present invention is a sample measuring apparatus, comprising:

a reagent holder for holding plural kinds of reagents;
a measurement unit for measuring a measurement sample, prepared from a sample and plural kinds of reagents held by the reagent holder, for a predetermined measurement item;
a display; and
a controller being configured to perform operations comprising:
    obtaining a measurable number of times indicating how many times the measuring unit is able to perform a measurement for the predetermined measurement item by using the plural kinds of reagents held by the reagent holder; and
    controlling the display so as to display a screen including a predetermined display area showing the obtained measurable number of times.

A third aspect of the present invention is a reagent information displaying method in a sample analyzer which comprises: a reagent holder for holding plural kinds of reagents; a measurement unit for measuring a measurement sample, prepared from a sample and plural kinds of reagents held by the reagent holder, for a predetermined measurement item; and a display, the method comprising steps of:

(a) obtaining a measurable number of times indicating how many times the measuring unit is able to perform a measurement for the predetermined measurement item by using the plural kinds of reagents held by the reagent holder; and (b) displaying, on the display, a screen including a predetermined display area showing the obtained measurable number of times.

A fourth aspect of the present invention is a computer program product for enabling a computer to control a display device in a sample measuring apparatus which comprises a reagent holder for holding plural kinds of reagents; and a measurement unit for measuring a measurement sample, prepared from a sample and plural kinds of reagents held by the reagent holder, for a predetermined measurement item, comprising:

a computer readable medium, and
software instruction, on the computer readable medium, for enabling the computer to perform predetermined operations comprising:
    obtaining a measurable number of times indicating how many times the measuring unit is able to perform a measurement for the predetermined measurement item by using the plural kinds of reagents held by the reagent holder; and
    controlling the display device so as to display a screen including a predetermined display area showing the obtained measurable number of times.

BRIEF DESCRIPTION OF THE DRAWINGS

FIG. 12 is a view showing a reagent detailed information display area of the reagent management screen shown in FIG. 11;

FIG. 28 is a view showing a reagent detailed information display area of the reagent management screen displayed on the display of the sample analyzer according to a variant of the present invention;

FIG. 29 is a schematic view showing a structure of measurement item database according to one embodiment of the present invention;

FIG. 30 is a schematic view showing a structure of reagent information database according to one embodiment of the present invention;

DETAILED DESCRIPTION OF THE EMBODIMENT

The embodiments embodying the present invention will now be described based on the drawings.

First, with reference to FIGS. 1 to 18, the structure of a sample analyzer 1 according to one embodiment of the present invention will be described. The sample analyzer 1 according to one embodiment of the present invention is an apparatus for optically measuring and analyzing the amount or degree of activity of a specific substance related to coagulation and fibrolytic function of the blood, and uses blood plasma for the sample. In the sample analyzer 1 according to the present embodiment, optical measurement (actual measurement) of the sample is performed using coagulation time method, synthetic substrate method, and immunoturbidimetric method. The coagulation time method used in the present embodiment is a measuring method of detecting the process the sample coagulates as change in transmitted light. The measurement items include PT (prothrombin time), APTT (activated partial thromboplastin time), Fbg (Fibrinogen content) or the like. The measurement item of the synthetic substrate method includes ATIII and the like, and the measurement item of the immunoturbidimetric method includes D dimer, FDP and the like.

Figure 1:
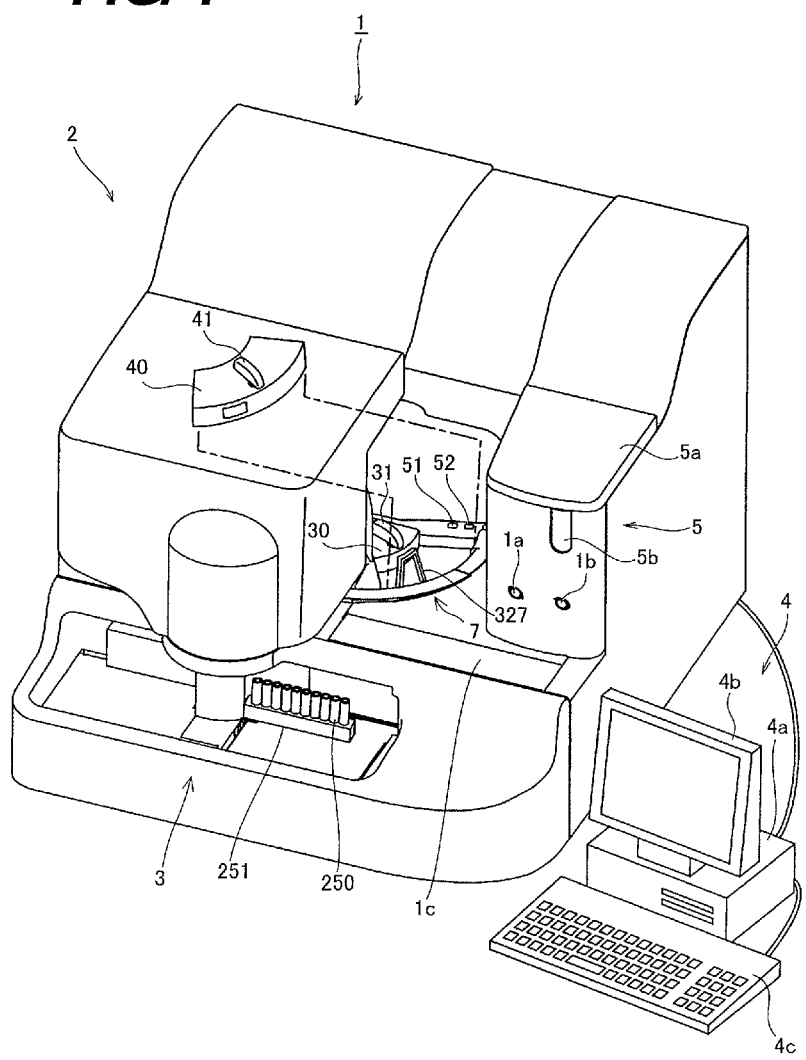
FIG. 1 is a perspective view showing an overall configuration of a sample analyzer according to one embodiment of the present invention.
Figure 2:
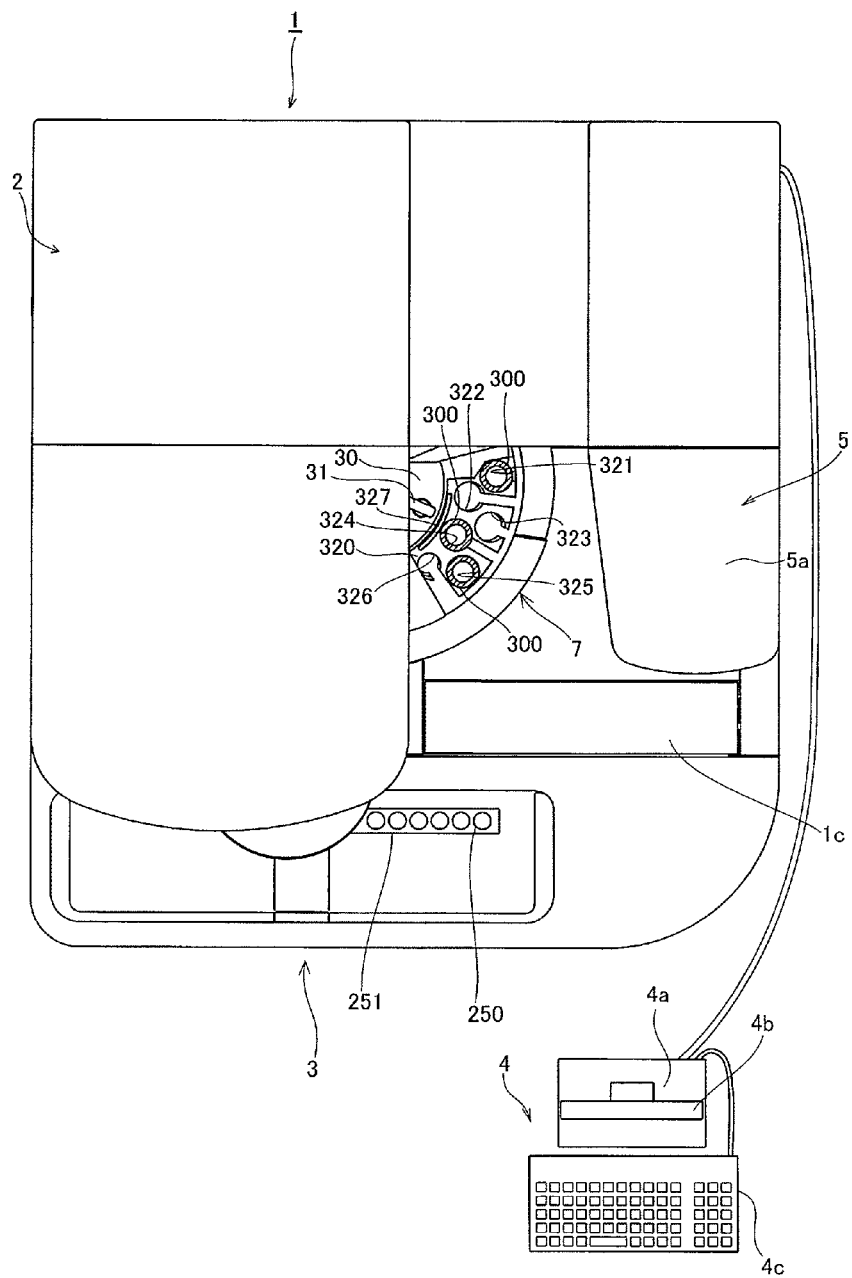
FIG. 2 is a plan view of the sample analyzer shown in FIG. 1.

As shown in FIGS. 1 and 2, the sample analyzer 1 is configured by a measurement mechanism unit 2, a sample conveyance mechanism unit 3 arranged on the front face side of the measurement mechanism unit 2, and a control device 4 electrically connected to the measurement mechanism unit 2. A cuvette inserting section 5 for inserting a cuvette 200 (see FIG. 4), which is the container of the sample when performing the measurement, is arranged in the measurement mechanism unit 2. An openable/closable lid 5a and a window 5b through which the interior of the cuvette inserting section 5 can be seen are formed in the cuvette inserting section 5. An emergency stop button 1a and a measurement start button 1b are arranged on the front face side of the cuvette inserting section 5. The lid 5a (see FIG. 1) is provided to insert the cuvette 200 into a hopper 161a (see FIG. 3) of a cuvette supply mechanism section 160, to be hereinafter described. The user is able to see the remaining amount of the cuvette 200 stored in the hopper 161a (see FIG. 3) through the window 5b. The emergency stop button 1a (see FIG. 1) has a function of stopping the measurement in time of emergency. The measurement start button 1b (see FIG. 1b) has a function of starting the measurement when pushed. The user thus can start the measurement immediately after inserting the cuvette 200. The measurement can also be started or stopped through operation of the control device 4.

As shown in FIGS. 1 and 2, the control device 4 consists of a personal computer 401 (PC) and the like, and includes a controller 4a, a display 4b and a keyboard 4c. The controller 4a has a function of transmitting an operation start signal of the measurement mechanism unit 2 to a controller 501 of the measurement mechanism unit 2, to be hereinafter described, and analyzing the optical information of the sample obtained by the measurement mechanism unit 2. The controller 4a is made up of CPU, ROM, RAM, or the like. The display 4b is provided to display information associated with interference substance (hemoglobin, milky fluid (fat), and bilirubin) present in the sample, as well as the analysis result obtained by the controller 4a.

Figure 6:
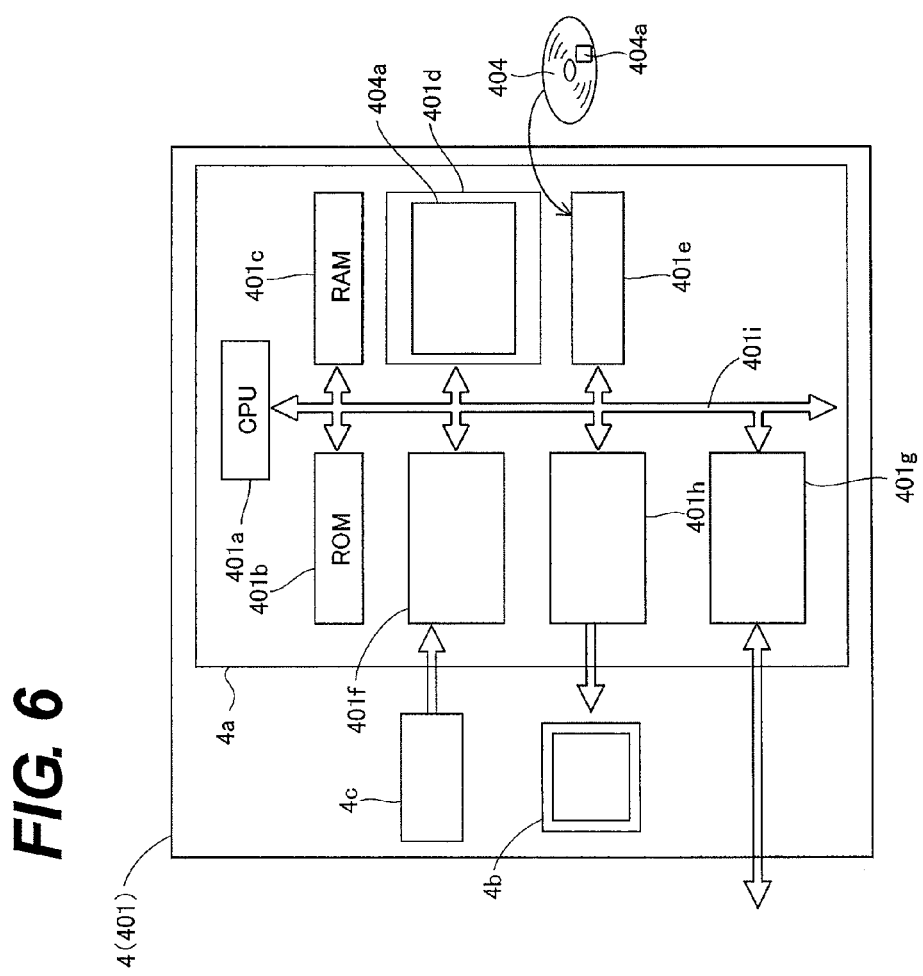
FIG. 6 is a block diagram showing a control device of the sample analyzer according to one embodiment of the present invention.

The configuration of the control device 4 will now be described. As shown in FIG. 6, the controller 4a is mainly configured by a CPU 401a, a ROM 401b, a RAM 401c, a hard disc 401d, a read-out device 401e, an input/output interface 401f, a communication interface 401g, and an image output interface 401h. The CPU 401a, the ROM 401b, the RAM 401c, the hard disc 401d, the read-out device 401e, the input/output interface 401f, the communication interface 401g, and the image output interface 401h are connected by a bus 401i.

The CPU 401a can execute computer programs stored in the ROM 401b and the computer programs loaded in the RAM 401c. The computer 401 serves as the control device 4 when the CPU 401a executes the application program 404a, as hereinafter described.

The ROM 401b is configured by mask ROM, PROM, EPROM, EEPROM, and the like, and is recorded with computer programs to be executed by the CPU 401a, data used for the same, and the like.

The RAM 401c is configured by SRAM, DRAM, or the like. The RAM 401c is used to read out the computer programs recorded on the ROM 401b and the hard disc 401d. The RAM 401c is used as a work region of the CPU 401a when executing the computer programs.

The hard disc 401d is installed with various computer programs to be executed by the CPU 401a such as operating system and application program, as well as data used in executing the computer program. The application program 404a for calculating the presence and the concentration of the interfering substance according to the present embodiment is also installed in the hard disc 401d. In the present embodiment, a table of a reagent master, a reagent lot master, a container master, and the like is also stored in the hard disc 401d. The hard disc 401d stores a measurement item information database 26 (see FIG. 29). As shown in FIG. 29, the measurement item database includes each field of measurement item that can be measured with the sample analyzer 1, reagent name used in each measurement item, and measurable number of times of each measurement item. The fields of the measurement item and the reagent name are registered in advance by the user. Thrombin reagent (manufactured by Sysmex Co.), Owen vernal buffer (manufactured by Sysmex Co.), exogenous enzyme, and the like are registered for the reagent name. In the field of the measurable number of times, the numerical value determined in the determination process of the measurable number of times, to be hereinafter described, is stored. The hard disc 401d stores a reagent information database 36 (see FIG. 30). As shown in FIG. 30, the reagent information database 36 is a relational database, and includes each field of holder number, reagent name, lot number, usable amount (remaining amount), remaining number of tests (usable number of times), set date, set time, and the like. Each record corresponds to one reagent of a plural of reagents placed in the reagent storing part 6. The controller 4a references the table of the reagent master, the reagent lot master, the container master, and the like, to be hereinafter described, stored in the hard disc 401d based on the barcode information read by a reagent barcode reader 350 to acquire the reagent information such as the holder number, the reagent name, the lot number, the kind of reagent container, and the expiration date of the reagent and store the same in the reagent information database 36. The reagent information stored in the reagent information database 36 is reflected on the display 4b by the controller 4a of the control device 4.

The read-out device 401e is configured by flexible disc drive, CD-ROM drive, DVD-ROM drive, and the like, and is able to read out computer programs and data recorded on a portable recording medium 404. The application program 404a according to the present embodiment is stored in the portable recording medium 404, wherein the computer 401 can read out the application program 404a from the portable recording medium 404, and install the application program 404a to the hard disc 401d.

The application program 404a is not only provided by the portable recording medium 404, and may be provided through an electrical communication line (wired or wireless) from external devices communicably connected with the computer 401 by the electrical communication line. For instance, the application program 404a may be stored in the hard disc of the server computer on the Internet, wherein the computer 401 can access the server computer to download the application program 404a and install the application program 404a in the hard disc 401d.

Operating system providing graphical user interface environment such as Windows (registered trademark) manufactured and sold by US Microsoft Co. is installed in the hard disc 401d. In the following description, the application program 404a according to the present embodiment is assumed to be operating on the operating system.

The input/output interface 401f is configured by serial interface such as USB, IEEE1394, RS-232C; parallel interface such as SCSI, IDE, IEEE1284; analog interface such as D/A converter, A/D converter, and the like. The keyboard 4c is connected to the input/output interface 401f, so that the user can input data to the computer 401 using the keyboard 4c.

The communication interface 401g is, for example, Ethernet (registered trademark) interface. The computer 401 can transmit and receive data with the measurement mechanism unit 2 using a predetermined communication protocol by means of the communication interface 401g.

The image output interface 401h is connected to the display 4b configured by LCD, CRT, or the like, and is configured to output the image signal corresponding to the image data provided from the CPU 401a to the display 4b. The display 4b displays the image (screen) according to the input image signal.

Figure 9:
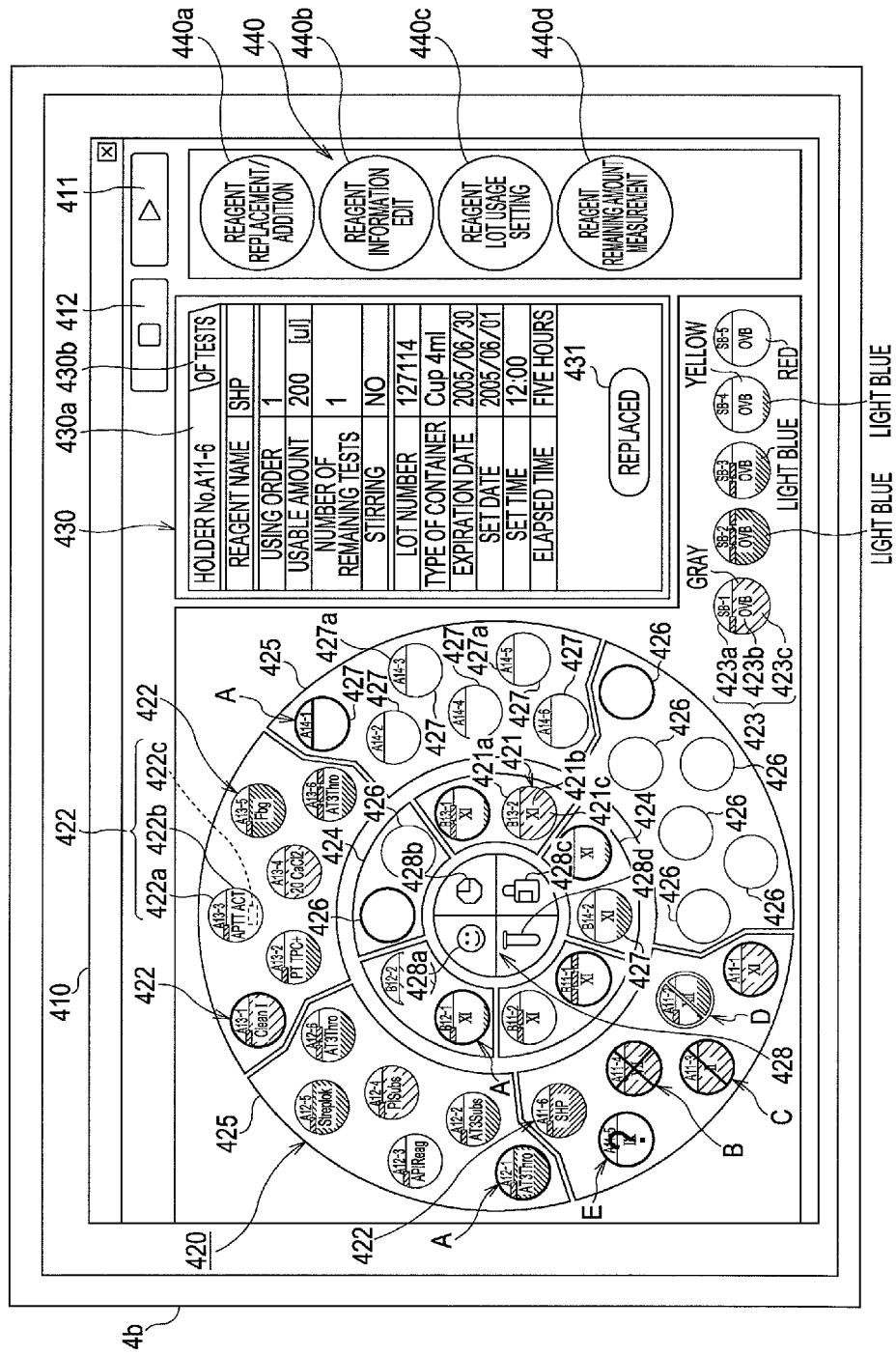
FIG. 9 is a view showing a reagent management screen displayed on the display of the sample analyzer according to one embodiment of the present invention.

In the present embodiment, the display 4b can display a reagent management screen 410 for displaying the arrangement of the reagents of the reagent storing part 6, to be hereinafter described, as shown in FIG. 9. The reagent management screen 410 includes a reagent arrangement display area 420, a reagent detailed information display area 430, and an operation means display area 440. The reagent management screen 410 also includes a measurement start button 411 for starting the measurement of the sample analyzer 1, and a measurement stop button 412 for stopping the measurement. The display 4b has a touch panel function, wherein the buttons and the like displayed on the reagent management screen 410 can be selected or operated by being directly touched by the user.

The reagent arrangement display area 420 displays, in a specifiable manner, a maximum of ten first reagent marks 421 displayed in correspondence to the arrangement state of the reagent arranged in a first reagent table 11 on the inner side, a maximum of thirty second reagent marks 422 displayed in correspondence to the arrangement state of the reagent arranged in a second reagent table 12 on the outer side, and a maximum of five diluting/cleaning fluid marks 423 displayed in correspondence to the arrangement state of the diluting fluid or the cleaning fluid. The first reagent mark 421 includes a position displaying portion 421a, arranged at the upper part of the first reagent mark 421, for displaying the position of the reagent, a reagent name displaying portion 421b, arranged at the central part of the first reagent mark 421, for displaying the reagent name, and an additional information displaying portion 422c, arranged at the lower part of the first reagent mark 421, for displaying the additional information showing the state of the reagent. Similarly, the second reagent mark 422 includes a position displaying portion 422a arranged at the upper part of the second reagent mark 422, a reagent name displaying portion 422b arranged at the central part of the second reagent mark 422, and an additional information displaying portion 421c arranged at the lower part of the second reagent mark 422. The diluting/cleaning fluid mark 423 includes a position displaying portion 423a, arranged at the upper part of the diluting/cleaning fluid mark 423, for displaying the position of the diluting/cleaning fluid, a fluid name displaying portion 423b, arranged at the central part of the diluting/cleaning fluid mark 423, for displaying the fluid name of the diluting/cleaning fluid, and an additional information displaying portion 423c, arranged at the lower part of the diluting/cleaning fluid mark 423, for displaying the additional information showing the state of the diluting fluid/cleaning fluid.

Figure 14:
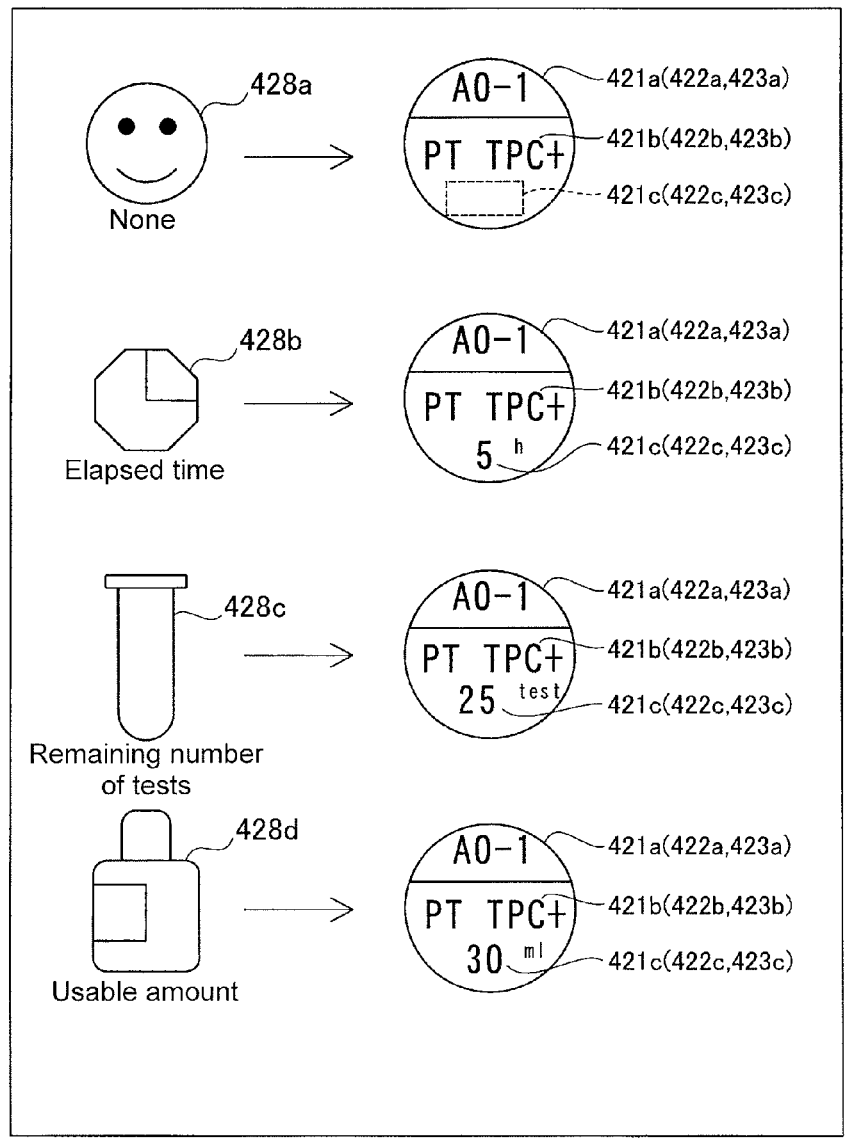
FIG. 14 is a view describing a switching display of the reagent name displaying portion of the reagent mark of the reagent management screen displayed on the display of the sample analyzer according to one embodiment of the present invention.
Figure 15:
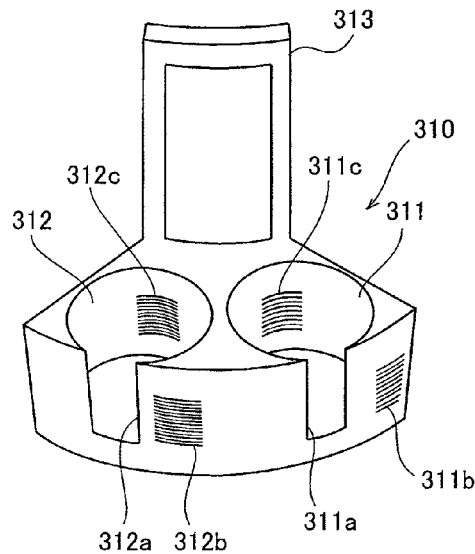
FIG. 15 is a perspective view showing a first reagent container rack according to one embodiment.

The additional information displaying portions 421c, 422c, and 423c can display any one of elapsed time information (unit: hour) from when the reagent is installed, measurable number of times (unit: test) of the measurement item that can be measured using the reagent, and reagent remaining amount (unit: ml). Which additional information to display or not display can be switched by the user. Specifically, a selection accepting region 428 including four icons is provided at the central portion of the reagent arrangement display area 420. The four icons are a no-additional information icon 428a, an elapsed time icon 428b, a reagent remaining amount icon 428c, and a remaining number of tests icon 428d. As shown in FIG. 14, when the no-additional information icon 428a is selected, switch is made to a state the additional information is not displayed in the additional information displaying portion 421c, 422c, and 423c of all reagent marks (first reagent mark 421, second reagent mark 422, and diluting/cleaning fluid mark 423). When the elapsed time icon 428b is selected, the elapsed time of the respective reagent is displayed in the additional information displaying portion 421c, 422c, and 423c of all reagent marks. Similarly, when the reagent remaining amount icon 428c is selected, the reagent remaining amount of the respective reagent is displayed in the additional information displaying portion 421c, 422c, and 423c of all reagent marks; and when the remaining number of tests icon 428d is selected, the remaining number of tests of the respective reagent is displayed in the additional information displaying portion 421c, 422c, and 423c of all reagent marks.

In the present embodiment, the specified first reagent mark 421, the second reagent mark 422, or the diluting/cleaning fluid mark 423 is displayed to be identifiable from the reagent marks or the diluting/cleaning fluid marks other than the specified reagent mark (first reagent mark 421, second reagent mark 422, or diluting/cleaning fluid mark 423). For instance, as shown in FIG. 9 and FIG. 13, the background with respect to the reagent name of the reagent name displaying portion (fluid name displaying portion) of the non-specified reagent mark is displayed in white (illustrated without hatching (diagonal lines)), whereas the background with respect to the reagent name (e.g., "SHP" of second reagent mark 422 of FIG. 9, I of FIG. 13) of the reagent name displaying portion of the specified reagent mark is displayed in blue (illustrated with hatching (diagonal lines)).

The positional information (holder number) of the reagent displayed in the position displaying portions 421a and 422a at the upper part of the first reagent mark 421 and the second reagent mark 422 is displayed by reading barcodes 311b, 312b (see FIG. 15) of a first reagent container rack 310 and barcodes 321b to 326b (see FIG. 16) of a second reagent container rack 320, to be hereinafter described, with the reagent barcode reader 350. The reagent name displayed in the reagent name displaying portions 421b and 422b at the central part of the first reagent mark 421 and the second reagent mark 422 is displayed with reference to the reagent master (table), to be hereinafter described, based on the value read by the reagent barcode reader 350 (see FIG. 5) from a barcode 300a of a reagent container 300 accommodating the reagent. The position displaying portion 423a of the diluting/cleaning fluid mark is constantly displayed since a holder 141 (see FIG. 5) of an emergency setting portion 140 for holding the diluting/cleaning fluid container (not shown) accommodating the diluting fluid or the cleaning fluid is fixed to the sample analyzer 1. The fluid name displaying portion 423b is displayed with reference to the reagent master (table) to be hereinafter described based on the value of reading the barcode (not shown) of the diluting/cleaning fluid container (not shown) accommodating the diluting fluid or the cleaning fluid with the reagent barcode reader 351.

The reagent remaining amount is calculated by the shape of the reagent container 300 and the height of the liquid level of the reagent stored in the reagent container 300 specified with reference to the container master (table) based on the value read by the reagent barcode reader 350 from the barcode 300a of the reagent container 300. The value (remaining number of tests) on how many more times the measurement (test) can be performed is also calculated from the value of the amount of reagent used in one measurement and the remaining amount. In the present embodiment, the calculated reagent remaining amount is indicator displayed with color or size (pattern) of the colored region at the background portion of the reagent name displaying portion (421b or 422b) of the reagent mark corresponding to the reagent.

Figure 13:
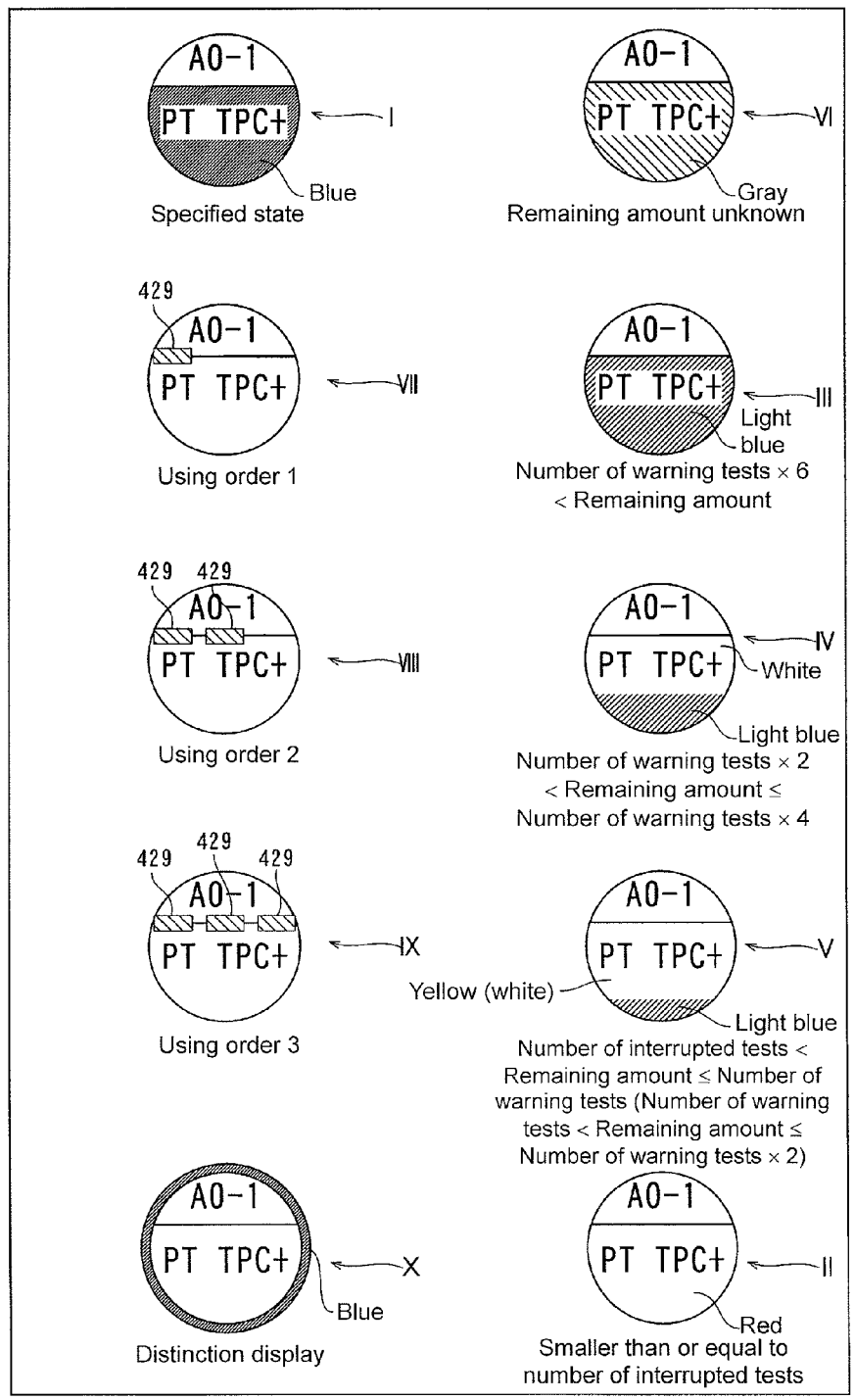
FIG. 13 is a view describing a display mode of the reagent mark of the reagent management screen displayed on the display of the sample analyzer according to one embodiment of the present invention.

As shown in FIG. 9 and FIG. 13, in the present embodiment, the reagent remaining amount is displayed in an identifiable manner by changing the color of the background and the size (pattern) of the colored region of the reagent name displaying portion and the additional information displaying portion for remaining amount≤number of interrupted tests, number of interrupted tests<remaining amount≤number of warning tests, number of warning tests<remaining amount≤number of warning tests×2, number of warning tests×2<remaining amount≤number of warning tests×4, number of warning tests×4<remaining amount≤number of warning tests×6, number of warning tests×6<remaining amount, and remaining amount unknown. The number of warning tests is the reference number of tests for issuing a warning when the reagent remaining amount becomes small (e.g., remaining amount enabling four measurements), and can be set by the user. The number of interrupted tests is the number of tests for interrupting the measurement when there is no reagent remaining amount (e.g., zero times).

In the details of the display of the remaining amount, the background of the reagent name displaying portion is changed to red when the reagent remaining amount is remaining amount≤number of interrupted tests (II of FIG. 13). The background of the reagent name displaying portion and the additional information displaying portion is changed to light blue when the reagent remaining amount is number of warning tests×6<remaining amount (III of FIG. 13). The upper part and the lower part of the background of the reagent name displaying portion and the additional information displaying portion are changed to white and light blue, respectively, and the indicator display is made such that the region displayed in light blue gradually reduces to thereby show that the reagent remaining amount is reducing in a stepwise manner when the reagent remaining amount is number of warning tests<remaining amount≤number of warning tests×2 (V of FIG. 13), number of warning tests×2<remaining amount≤number of warning tests×4 (IV of FIG. 13), or number of warning tests×4<remaining amount≤number of warning tests×6. The white portion is changed to yellow, which is a warning color, in the display of number of warning tests<remaining amount≤number of warning tests×2 when the reagent remaining amount is number of interrupted tests<remaining amount≤number of warning tests (V of FIG. 13). When the remaining amount is unknown (VI of FIG. 13), the background of the reagent name displaying portion and the additional information displaying portion is changed to gray. The remaining amount display in the reagent name displaying portion and the additional information displaying portion will be hereinafter described in detail.

The remaining amount of diluting fluid and cleaning fluid displayed in the remaining amount indicator (not shown) of the diluting fluid/cleaning fluid mark 423 is calculated by the shape of the diluting/cleaning fluid container specified with reference to the container master (table) and the height of the fluid level of the diluting fluid or the cleaning fluid accommodated in the diluting/cleaning fluid container based on the value read by the barcode reader 351 from the barcode (not shown) of the diluting/cleaning fluid container (not shown) accommodating the diluting fluid or the cleaning fluid. Similar to display of the remaining amount of the reagent, the calculated remaining amount of diluting/cleaning fluid is indicator displayed with color or the size of the colored region in the background portion of the fluid name displaying portion 423b and the additional information displaying portion 423c of the diluting/cleaning fluid mark 423.

If the same reagent exists in plurals, the order of use can be specified to the sample analyzer 1 by the user, which usage order is displayed in a distinguishable manner in the reagent mark. The usage order is displayed by distinguishing the first (VII of FIG. 13), the second (VIII of FIG. 13), and the third (IX of FIG. 13) by the number of indicators 429. The indicator 429 is not displayed for the reagent mark of the reagent which usage order is fourth or later.

Figure 5:
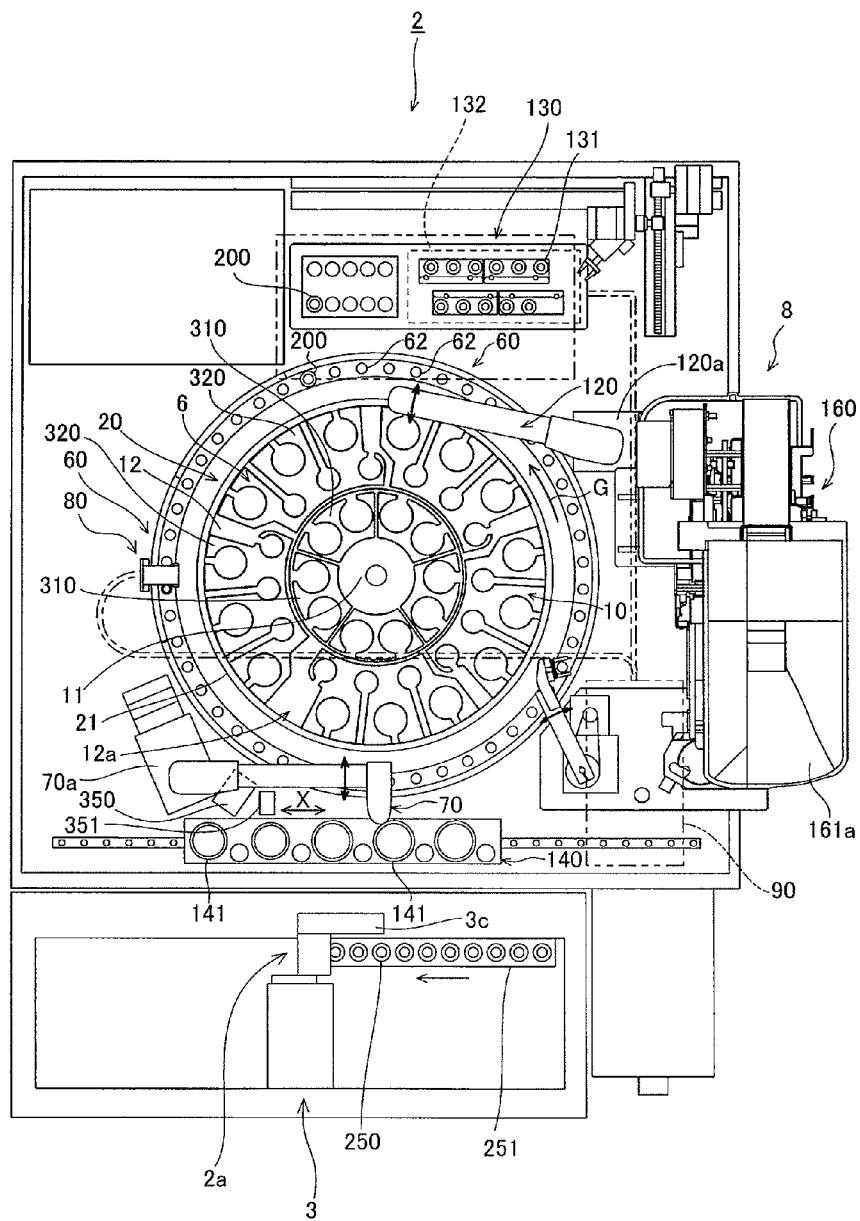
FIG. 5 is a plan view showing the interior of the measurement mechanism unit and the reagent storing part shown in FIG. 4.

The first reagent mark 421 is displayed by being divided by two for every second rack mark 424 corresponding to five first reagent container racks 320 (see FIG. 5) capable of holding two reagent containers 300 arranged in the first reagent table 11 (see FIG. 5). The second reagent mark 422 is displayed by being divided by sixes for every second rack mark 425 corresponding to five second reagent container racks 320 (see FIG. 5) capable of holding six reagent containers 300 arranged in the second reagent table 12 (see FIG. 5). In other words, at which position of which reagent container rack (first reagent container rack 310 or second reagent container rack 320) of which reagent table (first reagent table 11 or second reagent table 12) the reagent is placed can be checked in the reagent management screen 410.

If the reagent container rack is not arranged in the reagent table, a circular no-rack arrangement mark 426, where display is not made on the inner side, is displayed at a region corresponding to the portion where the reagent container rack is not arranged. If the first reagent container rack 310 or the second reagent container rack 320 is arranged in the first reagent table 11 or the second reagent table 12, and the reagent container 300 to be held in the reagent container rack is not present, a no-reagent arrangement mark 427 is displayed at a region corresponding to the portion where reagent is not arranged. The no-reagent arrangement mark 427 includes a position displaying portion 427a for displaying the positional information (holder number) of the portion not placed with the reagent. This will be hereinafter described in detail.

The mark positioned at the predetermined position of the first reagent mark 421, the second reagent mark 422, the no-rack arrangement mark 426, and the no-reagent arrangement mark 427 is displayed such that the outer periphery of the mark is a predetermined color (e.g., brown (illustrated with heavy line in FIG. 9)). The mark A where outer periphery is displayed in brown indicates that the reagent placed at the relevant position can be stirred. The reagent that requires stirring is placed at the position of the mark A where outer periphery is displayed in brown.

In the present embodiment, if the reagent that requires stirring is not arranged at the position of the mark A, which outer periphery is displayed in brown, an error arrangement mark B (e.g., red×mark) is displayed at the reagent mark of the reagent that requires stirring. An expired mark C (one red (illustrated with heavy line in the FIG. 9) diagonal line) is displayed at the reagent mark of the expired reagent. The sample analyzer 1 is configured such that the reagent corresponding to the reagent mark displayed with the error arrangement mark or the expired mark is not used for the measurement. A stabilization time expired mark D (e.g., one yellow (illustrated with outlined line in the FIG. 9) diagonal line) is displayed at the reagent mark of the reagent a predetermined time (e.g., eight hours) has elapsed from the set date and the set time of the reagent, to be described below. If the reading of the barcode 300a of the reagent container 300 by the reagent barcode reader 350 fails, a barcode reading error mark E (e.g., "?" mark) is displayed at the reagent mark of the reagent stored in the reagent container which reading failed.

The reagent detailed information display area 430 displays the detailed information (holder number, reagent name, using order, remaining usable amount (usable amount) of reagent, remaining number of tests, presence of stirring, lot number, kind of reagent container, expiration date of reagent, set date, set time, elapsed time, and the like) of the reagent corresponding to the specified first reagent mark 421 or the second reagent mark 422. More specifically, the positional information of the reagent displayed at the position displaying portion of the specified reagent mark is displayed in the field of "holder number". Similar to the reagent name displaying portion of the specified reagent mark, the reagent name specified with reference to the reagent master based on the value read from the barcode 300a of the reagent container 300 by the reagent barcode reader 350 is displayed in the field of "reagent name". The order of use in the measurement when the same reagent is arranged in plurals in the reagent table is displayed in the field of "using order". The remaining amount of the reagent corresponding to the specified reagent mark is displayed in the field of "usable amount". The value of dividing the "usable amount" by the reagent amount to be used for one measurement is displayed in the field of "remaining number of tests". Whether or not the reagent corresponding to the specified reagent mark needs to be stirred is displayed in the field of "stirring". The lot number specified with reference to the reagent lot master based on the value read from the barcode 300a of the reagent container 300 by the reagent barcode reader 350 is displayed in the field of "lot number". The kind of container specified with reference to the container master based on the value read from the barcode 300a of the reagent container 300 by the reagent barcode reader 350 is displayed in the field of "kind of container". The expiration date corresponding to the lot number specified with reference to the reagent lot master based on the value read from the barcode 300a of the reagent container 300 by the reagent barcode reader 350 is displayed in the field of "expiration date". The date and time at which the reagent corresponding to the specified reagent mark is set in the sample analyzer 1 are displayed in the field of "set date" and the field of "set time". The elapsed time from the "set time" at which the reagent is set in the sample analyzer 1 is displayed in the field of "elapsed time". The user can manage the reagent such as judging the replacement timing of the reagent by such detailed information of the reagent.

Figure 10:
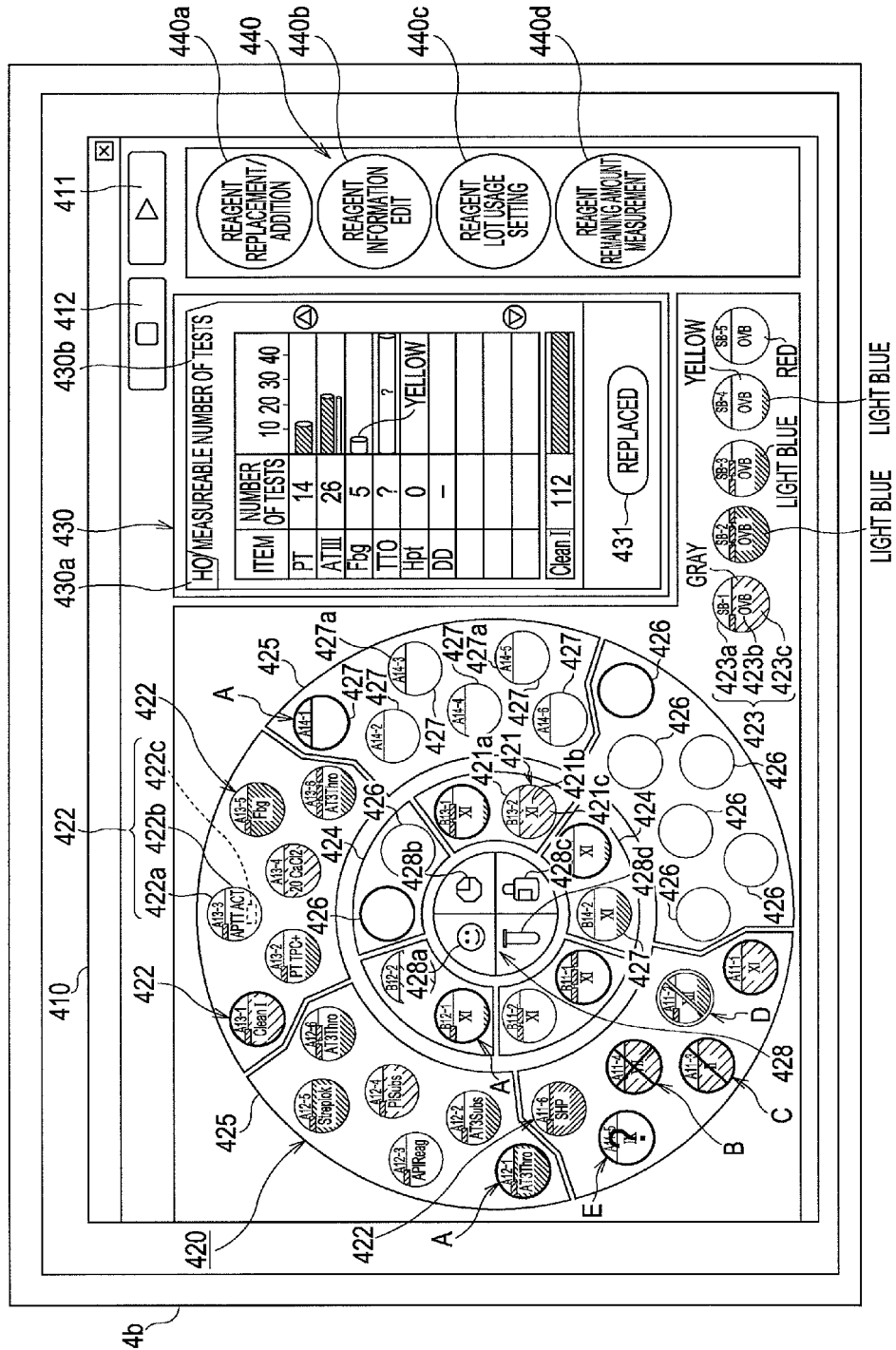
FIG. 10 is a view showing the reagent management screen displayed on the display of the sample analyzer according to one embodiment of the present invention.

As shown in FIG. 10 and FIG. 12, in the present embodiment, a reagent information tab 430a and a measurement item tab 430b are provided in the reagent detailed information display area 430, wherein the detailed information of the reagent is displayed in the reagent detailed information display area 430 when the reagent information tab 430a is selected. The information related to the measurement item is displayed in the reagent detailed information display area 430 when the measurement item tab 430b is selected. The detailed information of the reagent and the measurement item information are switch displayable, as needed, by the reagent information tab 430a and the measurement item tab 430b.

The measurement item information contains measurement item name information indicating the measurement item name registered in advance by the user, measurable number of times information indicating how many times each measurement item can be measured using the reagent installed at a current time point, and a graph representing the measurable number of times. If the same reagent is installed in plurals, the measurable number of times is calculated by the total of the remaining amount of such reagents. If the reagent that cannot be used for measurement or the reagent which remaining amount is unknown (reagent which remaining amount information is not stored in the hard disc 401d of the control device 4) exists in the plural of same reagents, the measurable number of times is calculated from the remaining amount of the reagent excluding the relevant reagent. The color of the graph is color-coding displayed by the measurable number of times. In other words, the graph of the measurement item which measurable number of times is large is displayed in light blue, and the graph of the measurement item which measurable number of times is less than a predetermined value is warning displayed in yellow. As the reagent with unknown remaining amount is contained in the reagent used for the measurement of the measurement item, the graph of the measurement item which measurable number of times cannot be calculated is displayed in gray, and a question mark "?" is displayed. As shown in FIG. 12, if the same reagent is installed in plurals, and the remaining amount of only some reagents is unknown, the measurable number of times by the reagent which remaining amount is known is displayed with a graph and a gray graph (see graph of measurement item "ATIII") is displayed adjacent to the relevant graph. With the display of such graph, the user can recognize that the reagent with unknown remaining amount exists in the reagent for measuring the measurement item. If the reagent necessary for measurement is not arranged in the reagent storing part 6 of the measurement item displayed in the reagent detailed information display area 430, "-(hyphen)" is displayed in the field of "number of tests" of the reagent detailed information display area 430 (see row of measurement item "DD"), and the entire row of the measurement item is displayed in gray.

Figure 11:
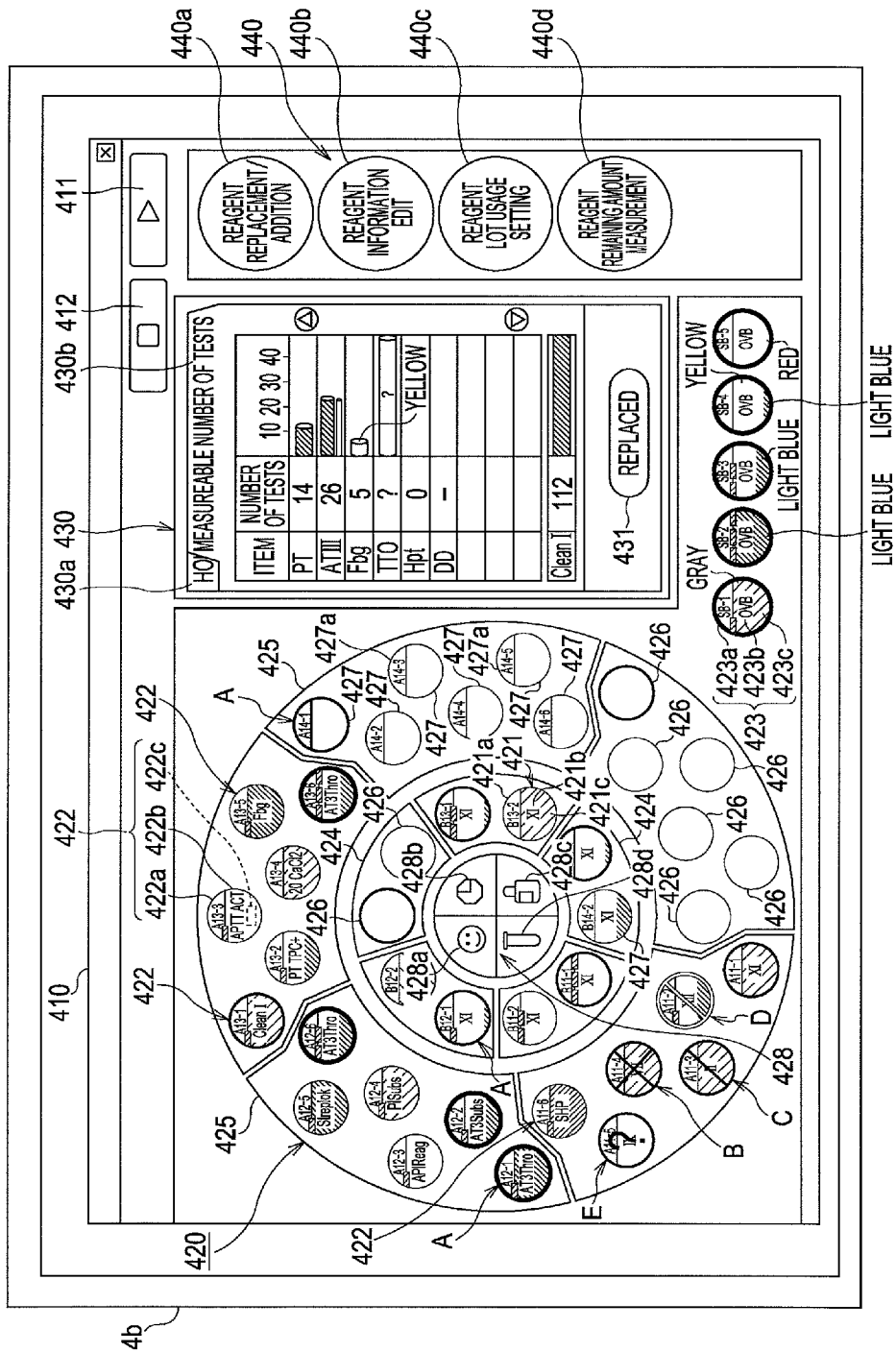
FIG. 11 is a view showing the reagent management screen displayed on the display of the sample analyzer according to one embodiment of the present invention.

The measurement item displayed in the reagent detailed information display area 430 can be selected by the user, wherein when the measurement item is selected, the reagent mark of the reagent used for the measurement of the selected measurement item is displayed in a distinguishable manner from other reagent marks. Specifically, as shown in FIG. 11, only the reagent mark of the reagent used for the measurement of the selected measurement item is displayed with the outer peripheral part surrounded with a heavy frame. In the example shown in FIG. 11, the outer peripheral part of "AT3Thro", "AT3Subs", and "OVB" or the reagent used for the measurement of the measurement item "ATIII" is displayed with a heavy frame when the measurement item "ATIII" is selected. With the measurement item selected and the outer peripheral part of the reagent mark of the reagent used for the measurement of the measurement item displayed with a heavy frame, the icons 428a to 428d of the selection accepting region 428 are selected and the additional information such as the remaining amount information is displayed in the reagent name displaying portion, or the reagent mark displayed with a heavy frame may be selected so that the detailed information of the reagent can be checked in the reagent detailed information display area 430.

The reagent detailed information display area 430 also includes "replaced" button 431. The "replaced" button 431 has a function of manually enabling the sample analyzer 1 to recognize that the reagent has been replaced when the replaced reagent is not recognized by the sample analyzer 1 although the reagent is replaced. The "set date" and the "set time" of the reagent detailed information display area 430 are updated to the date and time the "replaced" button 431 is pushed by pushing the "replaced" button 431.

The operation means display area 440 includes replacement/addition instructing button 440a for instructing replacement or addition of reagent, an edit button 440b for editing the reagent information, a reagent lot setting button 440c for assigning the reagent lot to the measurement item, and a reagent remaining amount check button 440d.

When the replacement/addition instructing button 440a is selected with the first reagent mark 421 or the second reagent mark 422 specified, the first reagent container rack 310 or the second reagent container rack 320 holding the reagent container 300 accommodating the reagent corresponding to the specified reagent mark is moved to a retrieving position at which it can be retrieved from the sample analyzer 1. When the reagent is to be added, the replacement/addition instructing button 440a is selected with the no-reagent arrangement mark 427 specified. The first reagent container rack 310 or the second reagent container rack 320 corresponding to the rack mark including the specified no-reagent arrangement mark is moved to the retrieving position. Similarly, the diluting fluid or the cleaning fluid can be replaced or added by selecting the replacement/addition button 440a with the diluting/cleaning fluid mark 423 specified.

A function of color-code displaying, so as to be identifiable by the user, a standby state from when the replacement/addition button 440a is pushed until the reagent container rack corresponding to the rack mark including the specified first regent mark 421, the second reagent ark 422, or the no-reagent arrangement mark 427 moves to the retrieving position when replacing or adding the reagent, and a retrievable state in which the reagent container rack can be retrieved to the outside from the retrieving position is also provided. The replacement and the addition of the reagent will be hereinafter specifically described in detail.

In the present embodiment, the detailed information of the reagent corresponding to the specified reagent mark can be edited by pushing the edit button 440b with the reagent mark specified. The reagent lot usage setting button 440c has a function of displaying a reagent lot usage setting dialogue (not shown) for setting whether each lot or the combination of lots is usable with respect to a plural of reagent lots or a combination of a plural of reagent lots for every measurement item. The reagent remaining amount check button 440d is provided to instruct the apparatus to detect the remaining amount when the reagent with unknown remaining amount (reagent which remaining amount information is not stored in the reagent information database 36 of hard disc 401d of control device 4) is installed.

Figure 3:
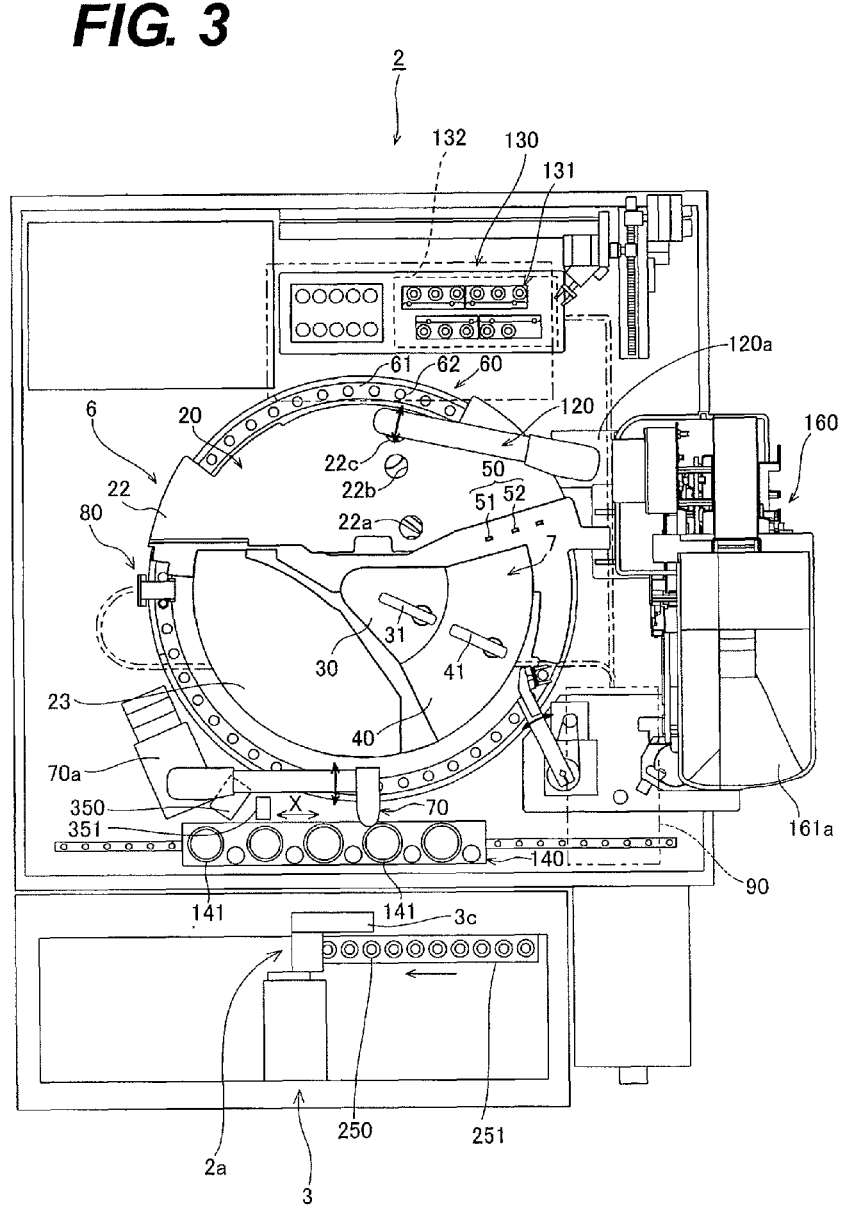
FIG. 3 is a plan view showing a measurement mechanism unit of the sample analyzer according to one embodiment of the present invention.

As shown in FIGS. 1 to 3, the conveyance mechanism unit 3 has a function of conveying a rack 251 mounted with a plural of (ten in the present embodiment) test tubes 250 accommodating a sample to an aspirating position 2a (see FIG. 3) of the measurement mechanism unit 2 to supply the sample to the measurement mechanism unit 2.

The measurement mechanism unit 2 is configured to acquire the optical information related to the supplied sample by performing an optical measurement with respect to the sample supplied from the conveyance mechanism unit 3. In the present embodiment, the optical measurement is performed on the sample dispensed into the cuvette 200 of the measurement mechanism unit 2 from the test tube 250 mounted in the rack 251 of the conveyance mechanism unit 3. As shown in FIG. 3, the measurement mechanism unit 2 includes the reagent storing part 6 for storing reagent, and the reagent replacing part 7 for replacing or adding the reagent.

Figure 7:
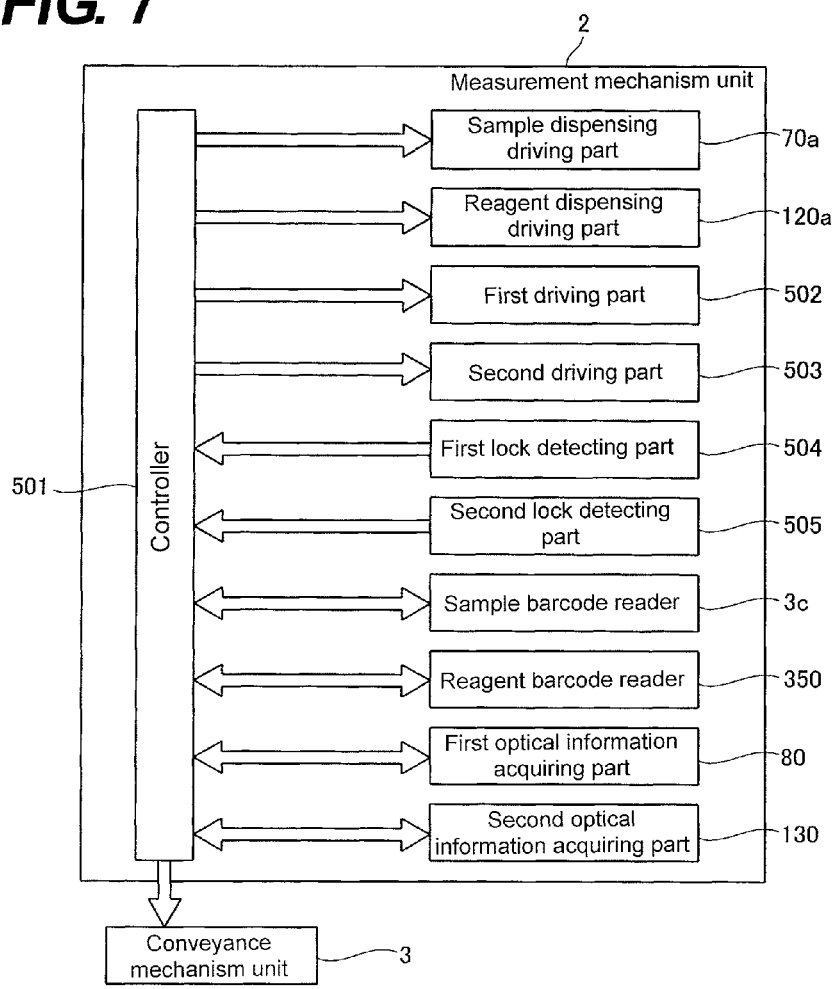
FIG. 7 is a block diagram showing a measurement mechanism unit of the sample analyzer according to one embodiment of the present invention.

As shown in FIG. 7, the measurement mechanism unit 2 includes a sample dispensing driving part 70a, a reagent dispensing driving part 120a, a first driving part 502, a second driving part 503, a first lock detecting part 504, a second lock detecting part 505, a reagent barcode reader 350, a sample barcode reader 3c, a first optical information acquiring part 80, a second optical information acquiring part 130, and a controller 501 electrically connected to the conveyance mechanism unit 3 and the like.

The sample dispensing driving part 70a includes a stepping motor 70b having a function of rotating a sample dispensing arm 70 (see FIGS. 3 and 5), to be hereinafter described, up and down, a drive circuit (not shown) for driving the stepping motor 70b, and a pump (not shown) for aspirating and dispensing the sample.

The reagent dispensing driving part 120a includes a stepping motor 120b having a function of rotating a reagent dispensing arm 120 (see FIGS. 3 and 5), to be hereinafter described, up and down, a drive circuit (not shown) for driving the stepping motor 120b, and a pump (not shown) for aspirating and dispensing the reagent.

The first driving part 502 includes a first stepping motor (not shown) having a function of rotating a first reagent table 11 (see FIG. 5), and a drive circuit (not shown) for driving the first stepping motor. The first reagent table 11 rotates by the amount corresponding to the number of pulses of the drive pulse signal provided from the controller 501 to the first driving part 502, and then stops.

Similarly, the second driving part 503 includes a second stepping motor (not shown) having a function of rotating a second reagent table 11 (see FIG. 5), and a drive circuit (not shown) for driving the second stepping motor. The second reagent table 12 rotates by the amount corresponding to the number of pulses of the drive pulse signal provided from the controller 501 to the second driving part 503, and then stops.

The controller 501 counts the number of pulses of the provided drive pulse signal to determine the rotatable movement amount of each reagent table 11, 12 from the origin position of the first reagent table 11 and the second reagent table 12 and control the rotatable movement of each reagent table 11, 12.

The first lock detecting part 504 has a function of detecting the lock state of the first lid 30 (see FIG. 3), and transmitting the lock signal to the controller 501 when locked.

Similarly, the second lock detecting part 505 has a function of detecting the lock state of the second lid 40 (see FIG. 3), and transmitting the lock signal to the controller 501 when locked.

Figure 4:
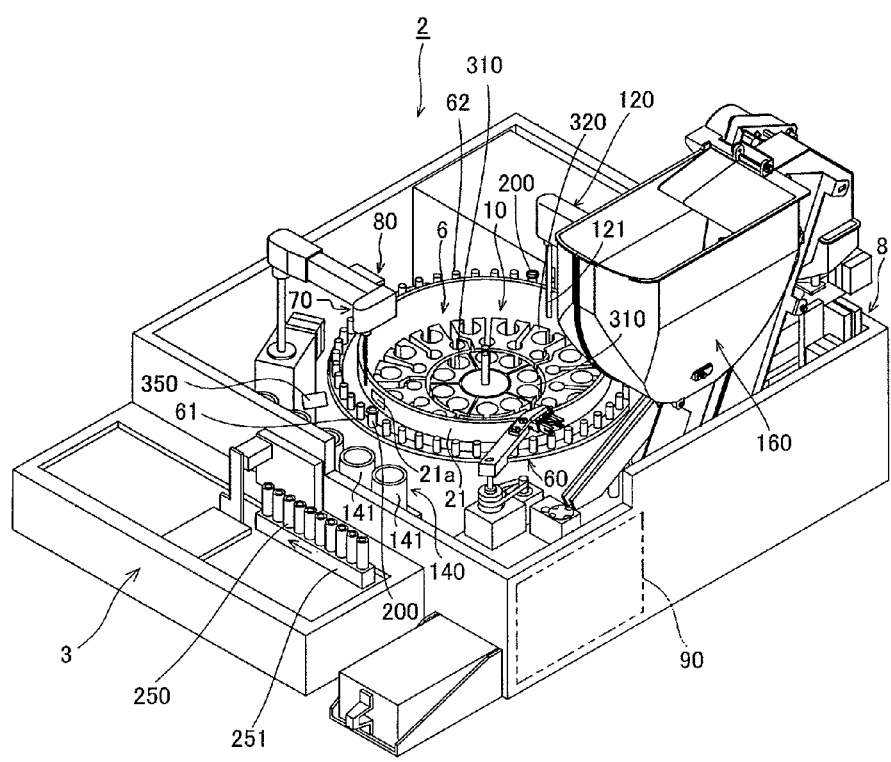
FIG. 4 is a perspective view showing the interior of the measurement mechanism unit and a reagent storing part of the sample analyzer according to one embodiment of the present invention.

The reagent barcode reader 350 has a function of reading each barcode of the first reagent table 11 and the second reagent table 12, and is arranged with a predetermined distance from the reagent storing part 6 near the side surface 21 of the reagent storing part 6 (see FIGS. 3 to 5). The reagent barcode reader 350 can transmit and receive data with the controller 501, and includes a drive circuit (not shown) for ON/OFF controlling the reagent barcode reader 350. The position of the reagent barcode reader 350 is always fixed.

The sample barcode reader 3c has a function of reading the barcode attached to a test tube 250 placed in the rack 251 conveyed by the conveyance mechanism unit 3, and is arranged to face the rack 251 conveyed by the conveyance mechanism unit 3 in the vicinity of the aspirating position 2a of the measurement mechanism unit 2 (see FIGS. 3 to 5). The sample barcode reader 3c can transmit and receive data with the controller 501, and includes a drive circuit (not shown) for ON/OFF controlling the sample barcode reader 3c. The position of the sample barcode reader 3c is always fixed.

Figure 8:
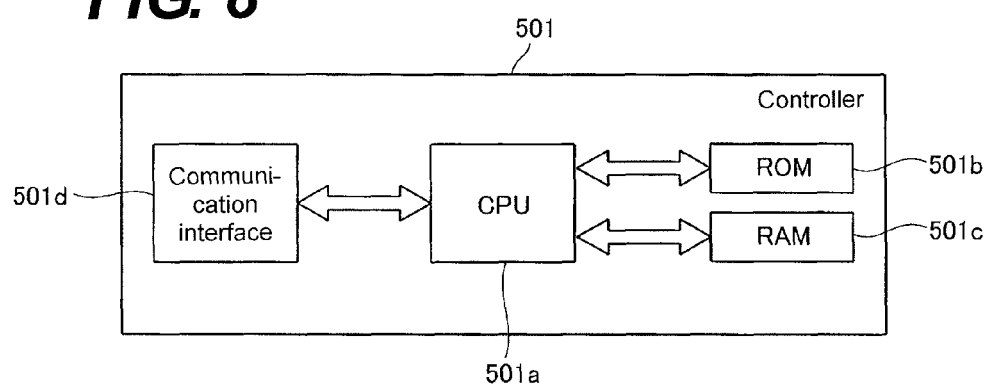
FIG. 8 is a block diagram showing a controller of measurement mechanism unit of the sample analyzer according to one embodiment of the present invention.

As shown in FIG. 8, the controller 501 is mainly configured by a CPU 501a, a ROM 501b, a RAM 501c, and a communication interface 501d.

The CPU 501a can execute the computer program stored in the ROM 501b and the computer program read out to the RAM 501c. The ROM 501b stores the computer program to be executed by the CPU 501a, the data used for the execution of the computer program, and the like. The RAM 501c is used to read out the computer program stored in the ROM 501b. The RAM 501c is used as a work region of the CPU 501a when executing the computer programs.

The communication interface 501d is connected to the control device 4, and has a function of transmitting optical information of the sample to the control device 4 and receiving signals from the controller 4a of the control device 4. The communication interface 501d also has a function of transmitting a command from the CPU 501a for driving each part of the conveyance mechanism unit 3 and the measurement mechanism unit 2.

As shown in FIG. 3, the measurement mechanism unit 2 includes the reagent storing part 6 for storing reagent, and the reagent replacing part 7 for replacing or adding the reagent.

The reagent storing part 6 is arranged to refrigerate the reagent container 300 accommodating the reagent to be added to the sample in the cuvette 200 at a low temperature (about 10° C.), and to convey the reagent container 300 in the rotating direction. The reagent is suppressed from alteration by being refrigerated at low temperature. As shown in FIGS. 3 to 5, the reagent storing part 6 includes a reagent conveying portion 10 (see FIGS. 4 and 5) for holding the reagent and rotatably conveying the same, and an outer wall portion 20 (see FIG. 3) arranged to cover the periphery and the upper side of the reagent conveying portion 10. The reagent conveying portion 10 holding the reagent is arranged in a refrigeration region formed by the outer wall portion 20, and the first lid 30 and the second lid 40 of the reagent replacing part 7, to be described below.

As shown in FIG. 5, the reagent conveying portion 10 includes the first reagent table 11 of circular shape, and, in the outer side of first reagent table 11 of circular shape, the second reagent table 12 of circular ring shape arranged concentrically with respect to the first reagent table 11. The first reagent table 11 and the second reagent table 12 are respectively configured such that the first reagent container rack 310 and the second reagent container rack 320 holding the reagent container 300 can be removably arranged. The outer wall portion 20 is configured by the side surface 21 (see FIG. 4), the upper surface 22 (see FIG. 3) fixed to the side surface 21, and the removable lid 23 (see FIG. 3). The reagent barcode reader 350 is arranged with a predetermined distance with the reagent storing part 6 near the side surface 21 (see FIG. 4) of the reagent storing part 6.

The first reagent table 11 and the second reagent table 12 are respectively configured so as to be rotatable in both the clockwise direction and the counterclockwise direction, each table being rotatable independent from each other. The first reagent container rack 310 and the second reagent container rack 320 for holding the reagent container 300 accommodating the reagent are respectively conveyed in the rotating direction by the first reagent table 11 and the second reagent table 12. When the reagent dispensing arm 120, to be hereinafter described, dispenses the reagent by conveying the reagent container 300 in the rotating direction, the reagent to be dispensed can be arranged close to the reagent dispensing arm 120.

A heat insulating material (not shown) is attached to the side surface 21 of the outer wall portion 20, and is configured to prevent the cold air in the reagent storing part 6 (refrigeration region) from escaping. As shown in FIG. 4, an openable/closable shutter 21a is arranged at a position facing the reagent barcode reader 350 of the side surface 21 of the outer wall portion 20. The shutter 21a is configured to open only when reading the barcode of the reagent container 300, the first reagent container rack 310, and the second reagent container rack 320 by the reagent barcode reader 350. Thus, the cold air in the reagent storing part 6 (refrigeration region) is suppressed from escaping outside.

As shown in FIG. 3, the upper surface 22 of the outer wall portion 20 includes three holes 22a, 22b, and 22c. The reagent stored in the reagent storing part 6 is aspirated by the reagent dispensing arm 120 through the three holes 22a, 22b, and 22c.

A semicircular opening forms in the reagent storing part 6 (refrigeration region) by detaching the lid 23 with the first lid 30 and the second lid 40. When starting the measurement in the sample analyzer 1 through the opening, the first reagent container rack 310 and the second reagent container rack 320 are arranged in the reagent storing part 6.

Figure 16:
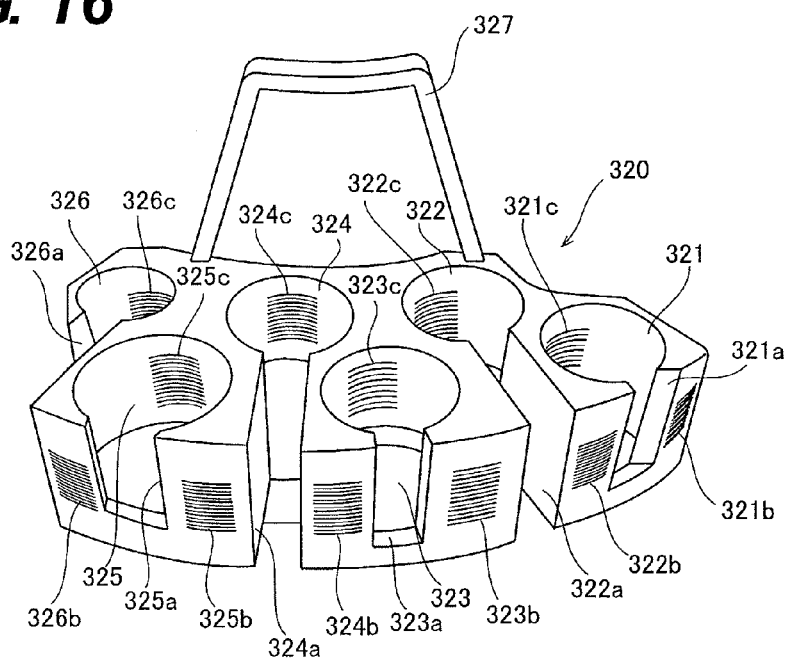
FIG. 16 is a perspective view showing a second reagent container rack according to one embodiment.
Figure 18:
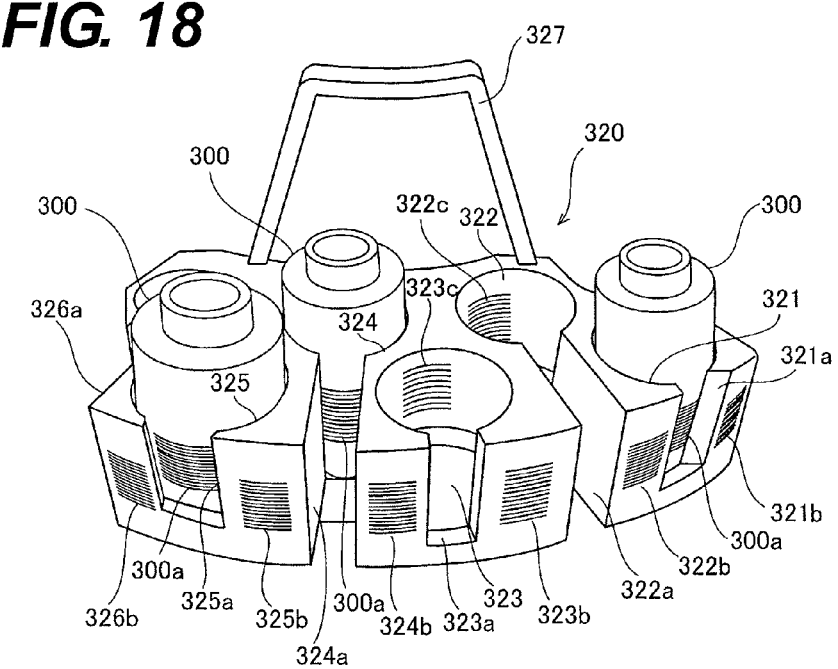
FIG. 18 is a perspective view showing a state in which the reagent container is held in the second reagent container rack shown in FIG. 16.

As shown in FIG. 5, five first reagent container racks 310 can be arranged in the first reagent table 11. The reagent container 300 is arranged in a circular ring shape in the five first reagent container racks 310. As shown in FIGS. 16 and 18, the first reagent container rack 310 includes two holders 311 and 312 for holding the reagent container 300, cutouts 311a and 312a respectively formed at the front surface side of the holders 311 and 312, and one grip 313 arranged projecting to the upper side. As shown in FIG. 16, the holders 311 and 312 are formed to a circular shape in plan view, and can hold the reagent container 300 by inserting a cylindrical reagent container 300. The barcodes 311b and 312b are respectively provided on the front surface side of the outer side surfaces of the holders 311 and 312, and barcodes 311c and 312c are respectively provided on the inner side surfaces of the holders 311 and 312.

Two holders 311 and 312 can hold, one at a time, a plural of reagent containers 300 accommodating various kinds of reagents to be added when preparing the measurement sample from the specimen. In other words, a maximum of ten (2×5=10) reagent containers 300 can be arranged in the first reagent table 11. Each cutout 311a and 312a is provided to read the barcodes 311c and 312c with the reagent barcode reader 350 (see FIG. 5). The grip 313 is gripped when taking out the first reagent container rack 310 from the reagent storing part 6.

Each barcode 311b and 312b includes positional information (holder number) for identifying the positions of the holders 311 and 312. The barcodes 311c and 312c include information (no reagent container information) indicating that the reagent container 300 held by the holders 311 and 312 does not exist. The barcode 300a of the reagent container 300 includes information for specifying the detailed information (information such as reagent name, kind of reagent container, lot number, and expiration date of reagent) of the reagent accommodated in the reagent container 300.

For instance, if the reagent container 300 is held by the holder 311, the barcode 311c is not read and the barcode 300a of the reagent container 300 is read. In other words, if the barcode 300a is read after reading the barcode 311b is read by the reagent barcode reader 350, the controller 4a recognizes that the reagent having the reagent information by the barcode 300a is held by the holder 311. In the reagent arrangement display area 420 of the reagent management screen 410, the first reagent mark 421 is displayed at the position corresponding to the holder 311. If the barcode 311c is read after the barcode 311b is read by the reagent barcode reader 350, the controller 4a recognizes that the reagent container 300 held by the holder 311 does not exist. In the reagent arrangement display area 420 of the reagent management screen 410, a no-reagent arrangement mark 427 is displayed at the position corresponding to the holder 311. If neither the barcode 300a nor the barcode 311c is read after the barcode 311b is read by the reagent barcode reader 350 (when the reagent container 300 is facing the side), the controller 4a recognizes the reading error and displays the barcode reading error mark E indicating that the reading failed in the display 4b. If the first reagent container rack itself is not arranged in the first reagent table 11, the reagent barcode 350 does not read the barcodes 311*b*, 312*b*, 311*c*, 312*c* of the first reagent container rack 310 and the barcode 300*a* of the reagent container 300. Thus, in the reagent arrangement display area 420 of the reagent management screen 410, a no-rack arrangement mark 426 is displayed on the first rack mark 424 corresponding to the portion not arranged with the first reagent container rack 310.

Figure 17:
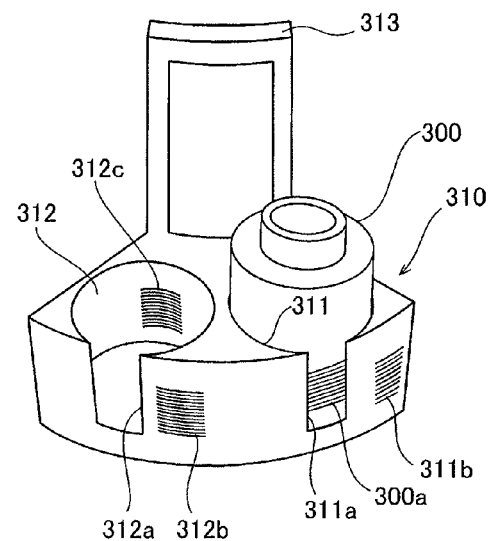
FIG. 17 is a perspective view showing a state in which the reagent container is held in the first reagent container rack shown in FIG. 15.
Figure 19:
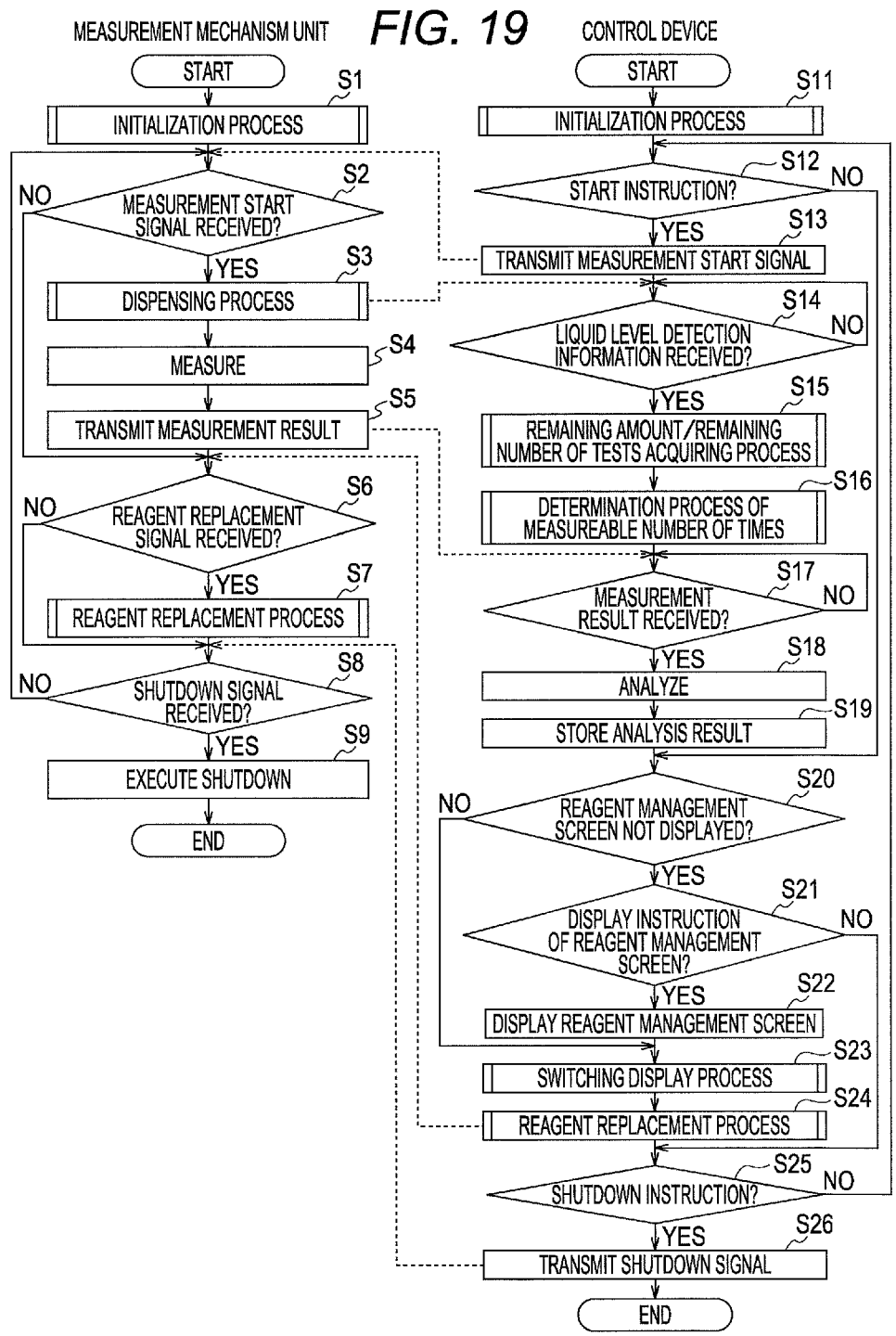
FIG. 19 is a flowchart describing the measurement process by the controller of the control device and the controller of the measurement mechanism unit of the sample analyzer according to one embodiment of the present invention.
Figure 20:
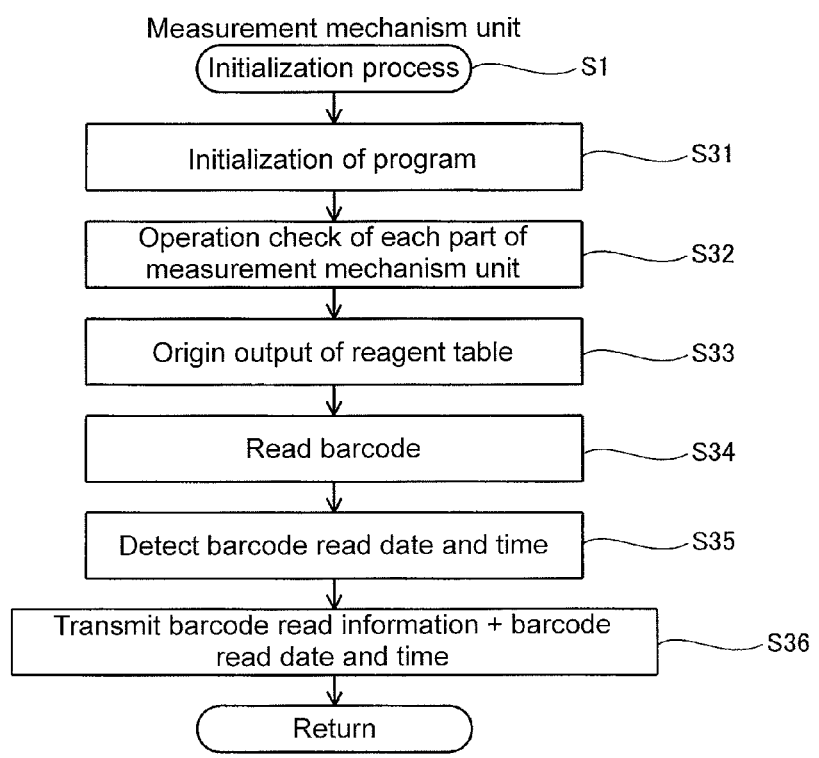
FIG. 20 is a flowchart for describing the initialization process of the measurement mechanism unit of the sample analyzer according to one embodiment of the present invention.

As shown in FIG. 5, five second reagent container racks 320 are arranged in the second reagent table 12. The reagent container 300 is arranged in a circular ring shape in the five reagent container racks 320. One location of the gap of the five locations of the second reagent container rack 320 adjacent to each other has an interval larger than the interval of the gap of other four locations. The barcodes 311*b* and 312*b* of the first reagent container rack 310 arranged in the first reagent table 11 positioned on the inner side of the second reagent table 12 and the barcode 300*a* of the reagent container 300 held by the first reagent container rack 310 are read by the reagent barcode reader 350 positioned on the outside of the reagent storing part 6 through the gap 12*a* having a large interval. As shown in FIGS. 17 and 19, the second reagent container rack 320 includes six holders 321 to 326 for holding the reagent container 300, cutouts 321*a* to 326*a* formed on the front surface side of the holders 321 to 326, and one grip 327 arranged projecting to the upper side. The holders 321 to 326 of the second reagent container rack 320 are formed to a circular shape in plan view, similar to the first reagent container rack 310, and can hold the reagent container 300 by inserting the cylindrical reagent container 300.

The barcodes 321*b* and 322*b* are formed on both sides of the cutout 321*a* on the front row side. Similarly, the barcodes 323*b* and 324*b*, and the barcodes 325*b* and 326*b* are formed on both sides of the cutout 323*a* and both sides of the cutout 325*a*. The barcodes 321*c* to 326*c* are formed on the inner side surfaces of the holders 321 to 326.

Each barcode 321*b* to 326*b* includes positional information (holder number) for identifying the position of the holder 321 to 326. The barcodes 321*c* and 326*c* include information (no-reagent container information) indicating that the reagent container 300 held by the holders 321 to 326 does not exist.

The reagent information or the no-reagent container information read by the reagent barcode reader 350 is stored in the reagent information database 36 of the hard disc 401*d* of the controller 4*a* in correspondence to the positional information (holder number). The information stored in the reagent information database 36 of the hard disc 401*d* is reflected on the reagent management screen 410 of the display 4*b* by the controller 4*a* of the control device 4.

The barcodes 311*b*, 312*b*, and 321*b* to 326*b* show the values of four digits. The first digit takes the value of "A" or "B", wherein "A" indicates that the reagent container 300 is arranged on the second reagent table 12, and "B" indicates that the reagent container 300 is arranged on the first reagent table 11. The second digit takes a value of "1" to "5", wherein "1" to "3" show three kinds of shapes of the second reagent container rack 320, and "4" and "5" show two kinds of shapes of the first reagent container rack 310. The third digit takes a value of "0" to "9", and indicates the number of the first reagent container rack 310 or the second reagent container rack 320. The fourth digit takes a value of "1" or "2" in the barcodes 311*b* and 312*b* of the first reagent container rack 310, wherein "1" and "2" show the holders 311 and 312, respectively. The fourth digit takes a value of "1" to "6" in the barcodes 321*b* to 326*b* of the second reagent container rack 320, wherein "1" and "6" show the holders 321 to 326. The value of the barcode (barcodes 311*b*, 312*b*, and 321*b* to 326*b*) is reflected on the position displaying portion 421*a* of the first reagent mark 421 of the reagent management screen 410, the position displaying portion 422*a* of the second reagent mark 422, or the position displaying portion 427*a* of the no-reagent arrangement mark 427, as shown in FIG. 9. If the value of the barcode is "A11-6", the container can be arranged on the second reagent table 12, it is the rack (second reagent container rack 320) corresponding to "1" of the three kinds, and is the sixth holder (holder 326) of the second reagent container rack 320 of the rack number 1. In other words, the first three digits of the values of the four digits specify the reagent container rack, and the last one digit specifies the position of the reagent in the relevant reagent container rack.

The reagent name of the detailed information is reflected on the reagent name displaying portions 421*b* and 422*b* of the first reagent mark 421 and the second reagent mark 422 of the reagent management screen 410. The no-reagent container information is reflected on the no-reagent arrangement mark 427. In other words, as shown in FIG. 9, the reagent name is displayed on the reagent name displaying portion 421*b* or 422*b* when the reagent is arranged, and no display is made on the reagent name displaying portion 421*b* or 422*b* when the reagent is not arranged. For instance, in FIG. 9, the reagent name "Streplok" is arranged at the reagent position "A12-5" and no reagent is arranged at the reagent position "A14-2".

As shown in FIGS. 1 and 2, the reagent replacing part 7 is arranged near the central part of the sample analyzer 1. In the present embodiment, the reagent replacing part 7 includes the first lid 30 and the second lid 40, which are detachable, with lock mechanisms 31 and 41, respectively, and a notifying portion 50 for notifying the conveying state of the first reagent table 11 and the second reagent table 12 to the user, as shown in FIG. 3.

The first lid 30 is configured to be detachable when replacing the reagent container 300 arranged on the first reagent table 11 (first reagent container rack 310). The lock mechanism 31 of the first lid 30 is locked to prevent the first lid 30 from detaching in time of normal use or after replacement or addition of the reagent is terminated, and is provided to have the controller 4*a* recognize that the replacement or the addition of the reagent at the first reagent table 11 is terminated.

The second lid 40 is configured to be detachable when replacing the reagent container 300 arranged on the second reagent table 12 (second reagent container rack 320). The lock mechanism 41 of the second lid 40 is locked to prevent the second lid 40 from detaching in time of normal use or after replacement of the reagent is terminated, and is provided to have the controller 4*a* recognize that the replacement or the addition of the reagent at the second reagent table 12 is terminated.

The notifying portion 50 includes two LED indicators 51 and 52. As shown in FIGS. 1 and 3, the two LED indicators 51 and 52 are arranged near the second lid 40, and are visible by the user from outside the sample analyzer 1. The LED indicators 51 and 52 can emit light in blue or red.

The LED indicator 51 has a function of notifying the user that the first reagent container rack 310 corresponding to the reagent of the first reagent table 11 specified on the reagent management screen 410 by the user moved to a retrieving position (lower side of first lid 30) where the reagent can be replaced.

The LED indicator 52 has a function of notifying the user that the second reagent container rack 320 corresponding to the reagent of the second reagent table 12 specified on the reagent management screen 410 by the user moved to a retrieving position (lower side of second lid 40) where the reagent can be replaced.

The user locks the first lid 30 or the second lid 40 after the replacement or the addition of the reagent is terminated, wherein the sample analyzer 1 is configured such that the reading of the barcode 300a of all the reagent containers 300 held by the first reagent container rack 310 or the second reagent container rack 320 holding the replaced reagent which is automatically performed. Thus, when one reagent is specified and the replacement of the reagent is instructed, the arrangement of the reagent after the replacement is correctly reflected on the reagent management screen 410 even when the reagent other than the specified reagent included in the same first reagent container rack 310 or the second reagent container rack 320 is replaced in addition to the specified reagent.

As shown in FIGS. 3 to 5, the measurement mechanism unit 2 includes a cuvette conveying part 60, a sample dispensing arm 70, a first optical information acquiring part 80, a lamp unit 90, a heating part 100, a cuvette transfer part 110, a reagent dispensing arm 120, a second optical information acquiring part 130, an emergency sample setting portion 140, a fluid part 150, and a cuvette supply mechanism section 160.

The cuvette conveying part 60 has a function of conveying the cuvette 200 to each portion of the sample analyzer 1. The cuvette conveying part 60 includes a cuvette conveying table 61 of circular ring shape arranged on the outer side of the second reagent table 12 of circular ring shape, and a plural of cylindrical cuvette holders 62 arranged with a predetermined spacing along the circumferential direction on the cuvette conveying table 61. The cuvette holder 62 is arranged to hold the cuvette 200 one at a time.

The sample dispensing arm 70 has a function of aspirating the sample accommodated in the test tube 250 conveyed to the aspirating position 2a by the conveyance mechanism unit 3, and dispensing the aspirated sample to the cuvette 200 held at the cuvette holder 62 of the cuvette conveying table 61. As shown in FIG. 4, the sample dispensing arm 70 is configured to move a pipette (not shown) in the up and down direction by a pulse control of the stepping motor (not shown). A sensor (not shown) for detecting the liquid level of the sample is arranged at the distal end of the pipette of the sample dispensing arm 70. Thus, when measuring the remaining amount of the reagent, the liquid level of the reagent, which remaining amount is to be measured, accommodated in the reagent container 300 is detected by the sensor. Thus, the height of the liquid level of the reagent in the reagent container 300 can be calculated by the number of pulses and the movement amount for one pulse for until the liquid level is detected.

The first optical information acquiring part 80 is configured to acquire optical information from the sample to measure the presence and the concentration of the interfering substance (milky fluid (fat), hemoglobin, and bilirubin) in the sample to which the reagent is added.

The acquisition of the optical information of the sample by the first optical information acquiring part 80 is performed before the optical measurement of the sample by the second optical information acquiring part 130. The first optical information acquiring part 80 acquires the optical information (information by transmitted light of the sample) from the sample in the cuvette 200 held at the cuvette holder 62 of the cuvette conveying table 61.

The first optical information acquiring part 80 is electrically connected to the controller 4a of the control device 4, and transmits the data (optical information) acquired by the first optical information acquiring part 80 to the controller 4a of the control device 4.

As shown in FIGS. 3 to 5, the reagent dispensing arm 120 is arranged to mix the reagent to the sample in the cuvette 200 by dispensing the reagent in the reagent container 300 mounted on the reagent storing part 6 to the cuvette 200. The reagent is added to the sample, which optical measurement by the first optical information acquiring part 80 is finished, to prepare the measurement sample.

The reagent dispensing arm 120 is configured to move the pipette 121 in the up and down direction by the pulse control of the stepping motor (not shown) when performing the dispensing operation. A sensor (not shown) for detecting the liquid level of the reagent when aspirating the reagent from the reagent container 300 is arranged at the distal end of the pipette 121 of the reagent dispensing arm 120. The height of the liquid level of the reagent in the reagent container 300 can be calculated by the number of pulses and the movement amount for one pulse for until the liquid level of the reagent is detected. The procedure for calculating the height of the liquid level of the reagent will be described in detail hereinafter.

The second optical information acquiring part 130 has a function of measuring optical information from the measurement sample. As shown in FIG. 5, the second optical information acquiring part 130 is configured by a measurement mounting portion 131 and a detecting portion 132 arranged on the lower side of the measurement mounting portion 131.

The second optical information acquiring part 130 is electrically connected to the controller 4a of the control device 4, and transmits the acquired data (optical information) to the controller 4a of the control device 4. Thus, in the control device 4, the data (optical information) transmitted from the second optical information acquiring part 130 is analyzed and displayed on the display 4b.

As shown in FIGS. 3 to 5, the emergency sample setting portion 140 is arranged to perform a sample analyzing process on the emergency sample. The emergency sample setting portion 140 is configured to cut in the emergency sample when the sample analyzing process on the sample supplied from the conveyance mechanism unit 3 is being performed. The emergency sample setting portion 140 is slidable in the X direction, and includes five holders 141 for holding container (not shown) accommodating the diluting fluid and the cleaning fluid. The container (not shown) accommodating the diluting fluid and the cleaning fluid is attached with a barcode (not shown). The barcode of the diluting fluid and the cleaning fluid is read by the barcode reader 351 while the emergency sample setting portion 140 is being sled in the X direction. The kind, arrangement, and the like of the diluting fluid and the cleaning fluid are displayed as the diluting/cleaning fluid mark 423 of the reagent management screen 410. As shown in FIGS. 1 and 2, a lid 1c is arranged on the front surface side of the replacing part 7 of the sample analyzer 1. The replacement or the addition of the container (not shown) accommodating the diluting fluid and the cleaning fluid is performed through the lid 1c.

The cuvette supply mechanism section 160 is configured such that a plural of cuvettes 200 randomly inserted to the hopper 161a by the user is sequentially supplied to the cuvette conveying part 60.

The analyzing operation of the sample of the sample analyzer 1 will be described in detail with reference to FIGS. 4 and 5. Here, the operation in the measurement using the coagulation time method will be described herein.

First, the initial setting of the sample analyzer 1 is performed by turning ON the powers of the measurement mechanism unit 2 and the control device 4 of the sample analyzer 1 shown in FIG. 4. The operation for returning the mechanism for moving the cuvette 200 and each dispensing arm (sample dispensing arm 70 and reagent dispensing arm 120) to the initial position, initialization of software stored in the controller 4a of the control device 4, and the like are performed.

The rack 251 mounted with the test tube 250 accommodating the sample is conveyed by the conveyance mechanism unit 3 shown in FIG. 5. The rack 251 is thereby conveyed to the position corresponding to the aspirating position 2a of the measurement mechanism unit 2.

A predetermined amount of sample is aspirated from the test tube 250 by the sample dispensing arm 70. The sample dispensing arm 70 is then moved to the upper side of the cuvette 200 held at the cuvette conveying table 61 of the cuvette conveying part 60. Thereafter, the sample is dispensed to the cuvette 200 by discharging the sample into the cuvette 200 of the cuvette conveying table 61 from the sample dispensing arm 70.

The cuvette conveying table 61 is rotated to convey the cuvette 200 dispensed with the sample to a position where measurement can be made by the first optical information acquiring part 80. The optical measurement on the sample is performed by the first optical information acquiring part 80, the optical information is acquired from the sample, and the optical information is transmitted to the controller 4a of the control device 4.

The reagent dispensing arm 120 is then driven to add the reagent in the reagent container 300 mounted on the reagent table (first reagent table 11 or second reagent table 12) to the sample in the cuvette 200. The measurement sample is then prepared.

The optical measurement is performed under a plural of conditions with respect to the measurement sample in the cuvette 200 by the detecting portion 132 of the second optical information acquiring part 130, so that the optical information (second optical information) is acquired from the measurement sample.

The acquired second optical information is sequentially transmitted to the controller 4a of the control device 4.

After the analysis by the controller 4a of the control device 4 is terminated, the obtained analysis result is displayed on the display 4b of the control device 4. The analyzing operation of the sample of the sample analyzer 1 is then terminated.

FIG. 19 is a flowchart for describing the measurement process flow of the control device and the measurement mechanism unit of the sample analyzer according to the present embodiment. The measurement process flow of the control device 4 and the measurement mechanism unit 2 of the sample analyzer 1 according to the present embodiment will be described below with reference to FIGS. 1, 3, 9, and 19.

First, after setting all the reagents in the reagent storing part 6, the user turns ON the power (not shown) of the measurement mechanism 2, so that the initialization of the controller 501 (initialization of the program) is performed and the operation check of each portion of the measurement mechanism unit 2 are performed in step S1. When the user turns ON the power (not shown) of the control device 4, initialization of the controller 4a (initialization of the program) is performed in step S11. After the initialization of the controller 501 is completed, the controller 501 requests for an initialization complete signal indicating the completion of initialization of the controller 4a, and controls the reagent barcode reader 350 to read the barcode of all the reagents set in the reagent storing part 6 and the barcode of the reagent rack when receiving the initialization complete signal. The read barcode information is transmitted from the controller 501 to the controller 4a, and stored in the hard disc 401d of the controller 4a.

In step S12, a menu screen (not shown) is displayed on the display 4b, wherein when the user pushes the start button displayed on the menu screen, a measurement start signal is transmitted from the controller 4a to the controller 501 in step S13. If the start button is not pushed in step S12, the process proceeds to step S20. The measurement item input screen for the user to input the measurement item is displayed on the display 4b by pushing the measurement item button (not shown) on the menu screen, so that the user can register the measurement item to be measured on the measurement item input screen.

In step S2, whether or not the measurement start signal is received is determined by the controller 501, wherein the process proceeds to step S3 if determined that the measurement start signal is received, and the process proceeds to step S6 if determined that the measurement start signal is not received.

In step S3, a process of dispensing the reagent to the sample dispensed to the cuvette 200 is performed, the liquid level is detected when aspirating the reagent to acquire the liquid level detection information, and the liquid level detection information is transmitted form the controller 501 to the controller 4a. In step S4, the sample dispensed with the reagent is measured by the first optical information acquiring part 80 and the second optical information acquiring part 130, and in step S5, the measurement result is transmitted from the controller 501 to the controller 4a.

In step S14, whether or not the liquid level detection information is received is determined by the controller 4a, wherein the process proceeds to step S15 if determined that the liquid level detection information is received, and the determination is repeated if determined that the liquid level detection information is not received. In step S15, the remaining amount/remaining number of tests acquiring process of the reagent is performed by the controller 4a. The remaining amount/remaining number of tests acquiring process will be hereinafter described, but is a process of calculating the reagent remaining amount based on the liquid level detection information, calculating the remaining number of tests based on the reagent remaining amount, and storing the reagent remaining amount and the remaining number of tests in the reagent information database 36 of the hard disc 401d. In step S16, the measurable number of times of the measurement item registered by the user is determined for every measurement item by the controller 4a. The determination process of the measurable number of times will be hereinafter described.

In step S17, whether or not the measurement result is received is determined by the controller 4a, wherein the process proceeds to step S18 if determined that the measurement result is received, and the determination is repeated if the measurement result is not received. In step S18, the measurement result is analyzed by the controller 4a, and in step S19, the analysis result is stored in the hard disc 401d.

In step S20, whether or not the reagent management screen 410 is displayed on the display 4b is determined by the controller 4a, wherein the process proceeds to step S21 if determined that the reagent management screen 410 is not displayed on the display 4b, and the process proceeds to step S23 if determined that the reagent management screen 410 is displayed on the display 4b. In step S21, whether or not a display instruction of the reagent management screen 410 is made (whether or not reagent button (not shown) for displaying the reagent management screen 410 of the menu screen) is determined by the controller 4a, wherein the process proceeds to step s22 if the display instruction of the reagent management screen 410 is made, and the process proceeds to step S25 if the display instruction of the reagent management screen 410 is not made. In step S22, the reagent management screen 410 is displayed by the controller 4a. When the reagent management screen 410 is displayed, the necessary information is reflected on the first reagent mark 421, the second reagent mark 422, and the reagent detailed information display area 430 displayed on the reagent management screen 410 based on the information stored in the reagent information database 36 by the controller 4a (see FIG. 9). The remaining amount of reagent is indicator displayed at the background portion of the reagent name displaying portion 421b of the first reagent mark 421 and the reagent name displaying portion 422b of the second reagent mark 422 displayed on the reagent arrangement display area 420 of the reagent management screen 410. In step S23, a switching display process in the reagent management screen 410 is executed by the controller 4a. The switching display process will be hereinafter described in detail.

In step S24, a reagent replacement process is performed. The reagent replacement process will be hereinafter described in detail.

In step S25, whether or not the instruction of shutdown is made is determined (whether or not the shutdown button (not shown) is pushed from the menu screen) by the controller 4a, wherein the process proceeds to step S26 if determined that the instruction of the shutdown is made, and the process returns to step S12 if determined that the instruction of the shutdown is not made. In step S26, the shutdown signal is transmitted from the controller 4a to the controller 501, the shutdown of the control device 4 is performed, and the process is terminated.

In step S6, whether or not the reagent replacement signal is received is determined by the controller 501, wherein the process proceeds to step S7 if determined that the reagent replacement signal is received, and the process proceeds to step S8 if determined that the reagent replacement signal is not received. In step S7, the reagent replacement process is performed by the controller 501. The reagent replacement process will be hereinafter described in detail.

Whether or not the shutdown signal is received is determined in step S8, wherein the process proceeds to step S9 if determined that the shutdown signal is received, and the process returns to step S2 if determined that the shutdown signal is not received. In step S9, the shutdown of the measurement mechanism unit 2 is performed, and the process is terminated.

In the measurement process flow of the measurement mechanism unit 2, step S3, step S4, and step S7 are parallel processed. In the measurement process flow of the control device 4, step S15, step S16, step S18, step 23, and step S24 are parallel processed.

The initialization process of the measurement mechanism unit 2 of the sample analyzer 1 according to the present embodiment will be described with reference to FIGS. 15 to 18, and 20.

First, in step S31, the initialization of the program is performed. In step S32, the operation check of each part of the measurement mechanism unit 2 is performed. In step S33, the origin output of the reagent table (first reagent table 11 and second reagent table 12) is performed. Thereafter, the barcodes 311b, 311c, 312b, 312c, 321b to 326b and 321c to 326c of the rack (first reagent container rack 310 and second reagent container rack 320) and the barcode 300a (see FIGS. 15 to 18) of the reagent container 300 held in the rack are read in step S34, and the barcode read date and time are detected in step S35. Subsequently, the barcode read information and the barcode read date and time are transmitted to the control device 4 in step S36, whereby the initialization process of the measurement mechanism unit 2 is terminated.

Figure 21:
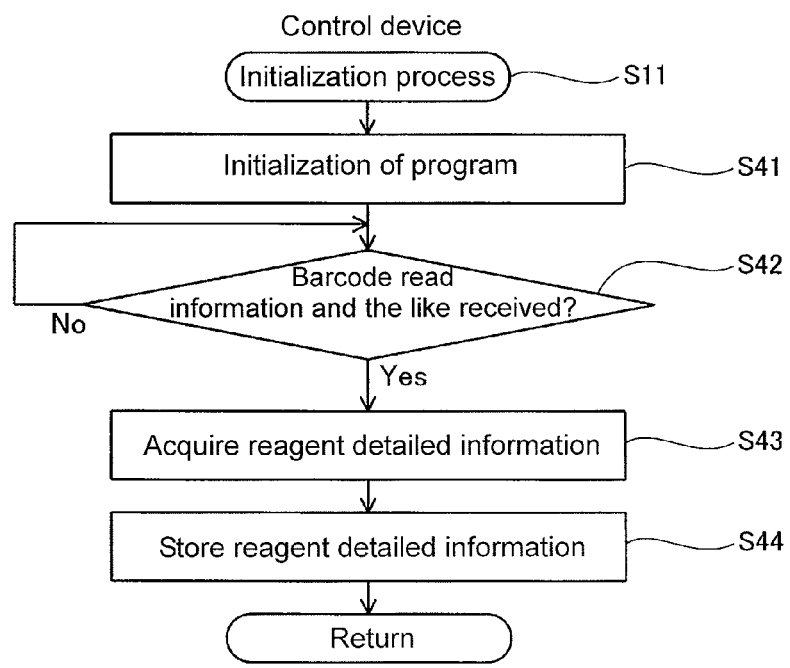
FIG. 21 is a flowchart for describing the initialization process of the control device of the sample analyzer according to one embodiment of the present invention.

The initialization process of the control device 4 of the sample analyzer 1 according to the present embodiment will be described with reference to FIG. 21.

First, in step S41, the initialization of the program is performed. In step S42, whether or not the barcode read information and the barcode read date and time are received from the controller 501 of the measurement mechanism unit 2 is determined. If the barcode read information and the barcode read date and time are not received, such determination is repeated. If the barcode read information and the barcode read date and time are received, the reagent detailed information (holder number, reagent name, set date and set time of reagent, and the like) are acquired based on the barcode read information, the reagent table, and the barcode read date and time in step S43. The controller 4a specifies the set date and the set time the reagent is set by the barcode read date and time. In step S44, the reagent detailed information is stored in the reagent information database 36 of the hard disc 401d. Since the information of the reagent placed in the reagent storing part 6 before shutting down the sample analyzer 1 at the previous time is stored in the reagent information database 36, if the same reagent is set at the position same as the previous time, the controller 4a saves the reagent detailed information of the reagent information database 36 as is with respect to such reagents. With respect to the reagent set at a position different from the previous time, or the regent newly set for this time, the reagent detailed information of the corresponding record in the reagent information database 36 is deleted, and the reagent detailed information newly acquired for this time is stored in the reagent information database 36. Thus, the reagent detailed information reflecting the arrangement state of the reagent in the reagent storing part 6 is stored in the reagent information database 36. The initialization process of the control device 4 is thereby terminated.

The dispensing process flow of the controller 501 of the measurement mechanism unit 2 of the sample analyzer 1 according to the present embodiment will be described with reference to FIGS. 3, 5, 22, and 23.

Figure 22:
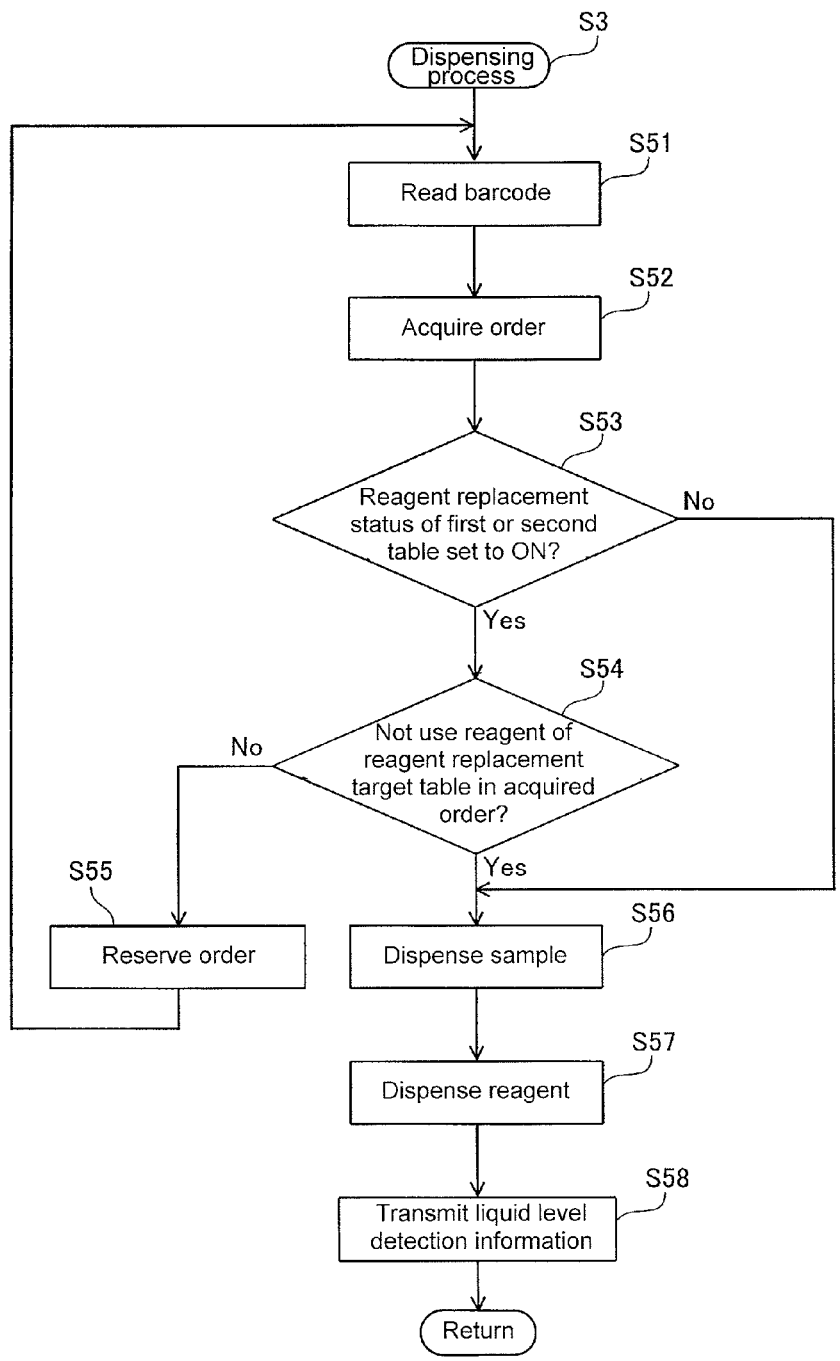
FIG. 22 is a flowchart for describing the dispensing process of the controller of the measurement mechanism unit of the sample analyzer according to one embodiment of the present invention.

First, the barcode attached to the test tube 250 accommodating the sample conveyed by the conveyance mechanism unit 3 is read by controlling the sample barcode reader 3c by the controller 501 in step S51 shown in FIG. 22. In step S52, the order is acquired based on the read barcode information by the controller 501, and the process proceeds to step S53. In step S53, whether or not the reagent replacement status of the first reagent table 11 or the second reagent table 12 is set to ON is determined by the controller 501. This process is performed by checking the status register incorporated in the drive circuit of the reagent replacement reagent table by the controller 501. If determined that the reagent replacement status of either the first reagent table 11 or the second reagent table 12 is set to ON in step S53, the process proceeds to step S54. If determined that neither reagent replacement status is set to ON in step S53, the process proceeds to step S56. The order will be described below. The order is the information including the analyzing items corresponded to the information specifying the sample. The order is registered in a host computer (not shown) connected to the control device 4, or is stored through manual input by the user to the control device 4. After acquiring the barcode information of the sample, the control device 4 searches the relevant order from the order stored inside, or inquires the host computer with the sample ID as the key to acquire the order. The order acquired by the control device 4 is transmitted from the controller 4a of the control device 4 to the controller 501 of the measurement mechanism unit 2, and the controller 501 acquires the order.

Figure 23:
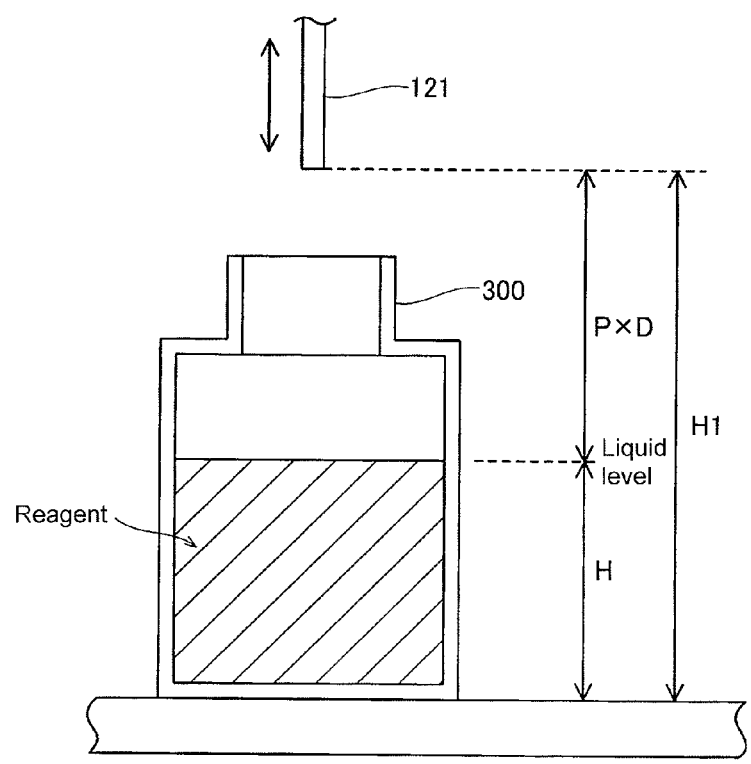
FIG. 23 is a conceptual view describing the calculation method of the reagent remaining amount.

In step S56, the sample dispensing driving part 70a is controlled according to the order by the controller 501, the sample stored in the test tube 250 conveyed by the conveyance mechanism unit 3 is aspirated and the aspirated sample is dispensed into the cuvette 200 held by the cuvette holder 62 of the cuvette conveying table 61 by the sample dispensing arm 70. In step S57, the reagent dispensing driving part 120a is controlled by the controller 501, and the reagent is aspirated through the holes 22a, 22b, or 22c (see FIG. 3) of the outer wall portion 20 of the reagent storing part 6 and the aspirated reagent is dispensed to the cuvette 200, which warming is completed, by the reagent dispensing arm 120. As shown in FIG. 23, in step S57, the pipette 121 of the reagent dispensing arm 120 is moved to the lower side from the initial position (height H1) for aspirating the reagent. The pipette 121 is driven by the stepping motor, and is moved by the movement distance D every time one pulse is input to the stepping motor. The liquid level of the reagent is detected by the sensor arranged at the distal end of the pipette 121. The number of pulses P, which is one liquid level detection information, of the case where the sensor detects the liquid level of the reagent is acquired. The acquired liquid level detection information is transmitted to the control device 4 by the controller 501 in step S58.

If determined that the reagent replacement status of either the first reagent table 11 and the second reagent table 12 is set to ON by the controller 501 in step S53, whether or not the analyzing item specified in the acquired order uses the reagent of the reagent replacement target table is determined. If determined that the analyzing item specified in the acquired order does not use the reagent of the reagent replacement target table in step S54, the process proceeds to steps S56, S57, and the processes described above are performed. If determined that the analyzing item specified in the acquired order use the reagent of the reagent replacement target table, the acquired order is reserved in step S55. The steps S51 to S55 are repeated until determined that the analyzing item specified in the acquired order does not use the reagent of the reagent replacement target table. In the reserved order, if determined that the analyzing item specified in the acquired order does not use the reagent of the reagent replacement target table, the processes of steps S56, S57, S58 are executed in order.

The process of calculating the remaining amount and the remaining number of tests of the reagent is then described with reference to FIGS. 23 and 24.

Figure 24:
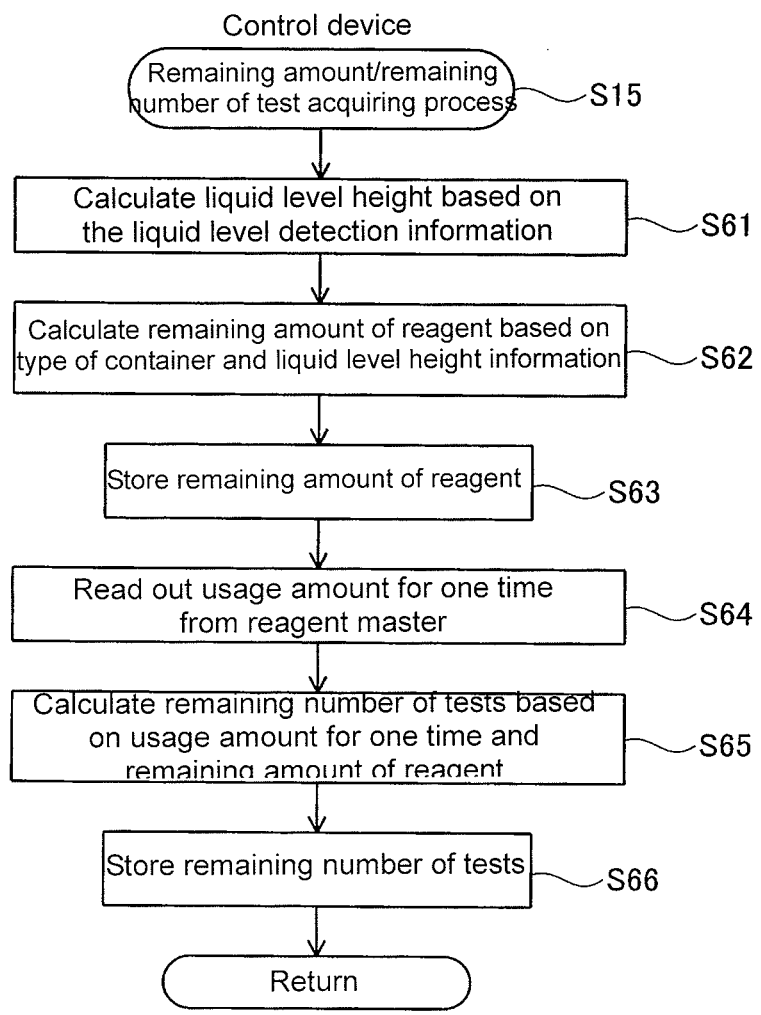
FIG. 24 is a flowchart for describing the reagent remaining amount/remaining number of tests acquiring process of the reagent by the control device of the sample analyzer according to one embodiment of the present invention.

In step S61 shown in FIG. 24, the height of the liquid level is calculated based on the received liquid level detection information by the controller 4a. The liquid level detection information includes the number of pulses P and the distance D (see FIG. 23) of the case where the liquid level is detected. The container master is referenced by the controller 4a to specify the reagent container based on the container ID and acquire the inner surface area S in the horizontal direction of the specified reagent container. The reagent name is acquired based on the reagent ID with reference to the reagent master. The height H of the liquid level is obtained by the following equation (1) by the controller 4a.

$$H(\text{height of liquid level})=H1(\text{height of initial position})-P(\text{number of pulses})\times(\text{movement distance of one pulse}) \quad (1)$$

In step S62, the remaining amount T of the reagent is calculated by the following equation (2) by the controller 4a from the inner surface area S of the acquired reagent container and the acquired height H of the liquid level of the reagent.

$$T(\text{remaining amount})=H(\text{height of liquid level})\times S(\text{inner surface area of reagent container}) \quad (2)$$

In step S63, the controller 4a stores the calculated remaining amount T of the reagent in the field of "usable amount" of the corresponding record in the reagent information database 36 of the hard disc 401d. If the data of the reagent remaining amount is already stored in the field of "usable amount" of the record, the controller 4a deletes such data and newly stores the reagent remaining amount T calculated for this time.

In step S64, the usage amount of the reagent to be used for one measurement is read by the controller 4a by referencing the reagent master. In step S65, the remaining number of tests is calculated based on the usage amount of the reagent to be used for one measurement and the remaining amount T of the reagent stored in the reagent information database 36, and in step S66, the calculated remaining number of tests is stored in the field of "remaining number of tests" of the corresponding record in the reagent information database 36 of the hard disc 401d. If the data of the remaining number of tests is already stored in the field of "remaining number of tests" of the record, the controller 4a deletes the data and newly stores the remaining number of tests calculated for this time. Steps S61 to S66 are repeated every time the measurement is performed.

The process of determining the measurable number of times for every measurement item will now be described with reference to FIG. 31 and the like.

Figure 31:
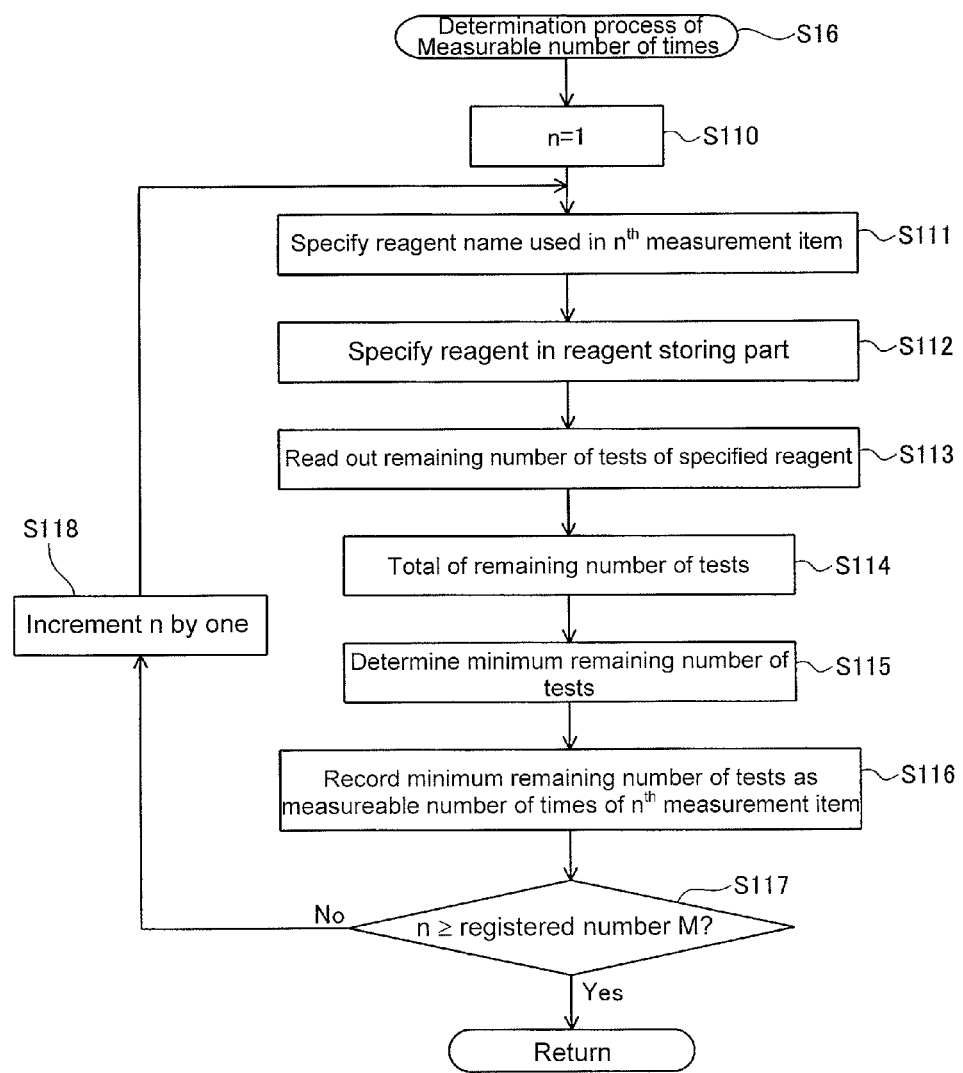
FIG. 31 is a flowchart describing a determination process of the measurable number of times by the control device according to one embodiment of the present invention.

In step S110 shown in FIG. 31, the counter n is set to an initial value 1 by the controller 4a. In step S111, the controller 4a specifies the reagent name used in the nth measurement item of the measurement items registered as a measurement target in advance by the user with reference to the measurement item database 26 of the hard disc 401d. For instance, if the nth measurement item is "ATIII", exogenous enzyme, color fixing agent, and Owen vernal buffer solution (manufactured by Sysmex Co.) are specified. In step S112, the controller 4a specifies the reagent corresponding to the reagent name specified in step S111 of a plural of reagents arranged in the reagent storing part 6.

In step S113, the controller 4a reads out the remaining number of tests of each reagent specified in step S112 from the reagent information database 36 of the hard disc 401d. In step S114, the remaining number of tests is totaled for every kind of reagent specified in step S111 by the controller 4a. For instance, if the nth measurement item is "ATIII", the total of the remaining number of tests of the exogenous enzyme, the total of the remaining number of tests of the color fixing agent, and the total of the remaining number of tests of the Owen vernal buffer (manufactured by Sysmex Co.) are calculated. For instance, if three exogenous enzymes are arranged in the reagent storing part 6, each remaining number of tests of the three exogenous enzymes is totaled when calculating the remaining number of tests of the exogenous enzyme.

In step S115, the minimum remaining number of tests of the total of the remaining number of tests calculated in step S114 is determined by the controller 4a. For instance, if the total of the remaining number of tests of the exogenous enzyme is 150 times, the total of the remaining number of tests of the color fixing agent is 170 times, and the total of the remaining number of tests of the Owen vernal buffer (manufactured by Sysmex Co.) is 300 times, the 150 times of the exogenous enzyme is determined as the minimum remaining number of tests. In step S116, the minimum remaining number of tests determined in step S115 is stored in the measurement item database 26 of the hard disc 401d as the measurement number of times of the nth measurement item by the controller 4a. For instance, if the nth measurement item is "Fbg", it is stored in the field of "measurable number of times" of the "Fbg" record of the measurement item database 26.

In step S117, whether or not the counter n is greater than or equal to the number of measurement items M registered by the user in advance is determined by the controller 4a, and the process returns if the counter n is greater than or equal to the registered number M. If the counter n is smaller than the registered number M, the process proceeds to step S118, the counter n is incremented by one, and the process returns to step S111. The processes of steps S111 to S118 are repeated. The measurable number of times using the reagent arranged in the reagent storing part 6 is determined for every measurement item, and stored in the measurement item database 26.

Figure 25:
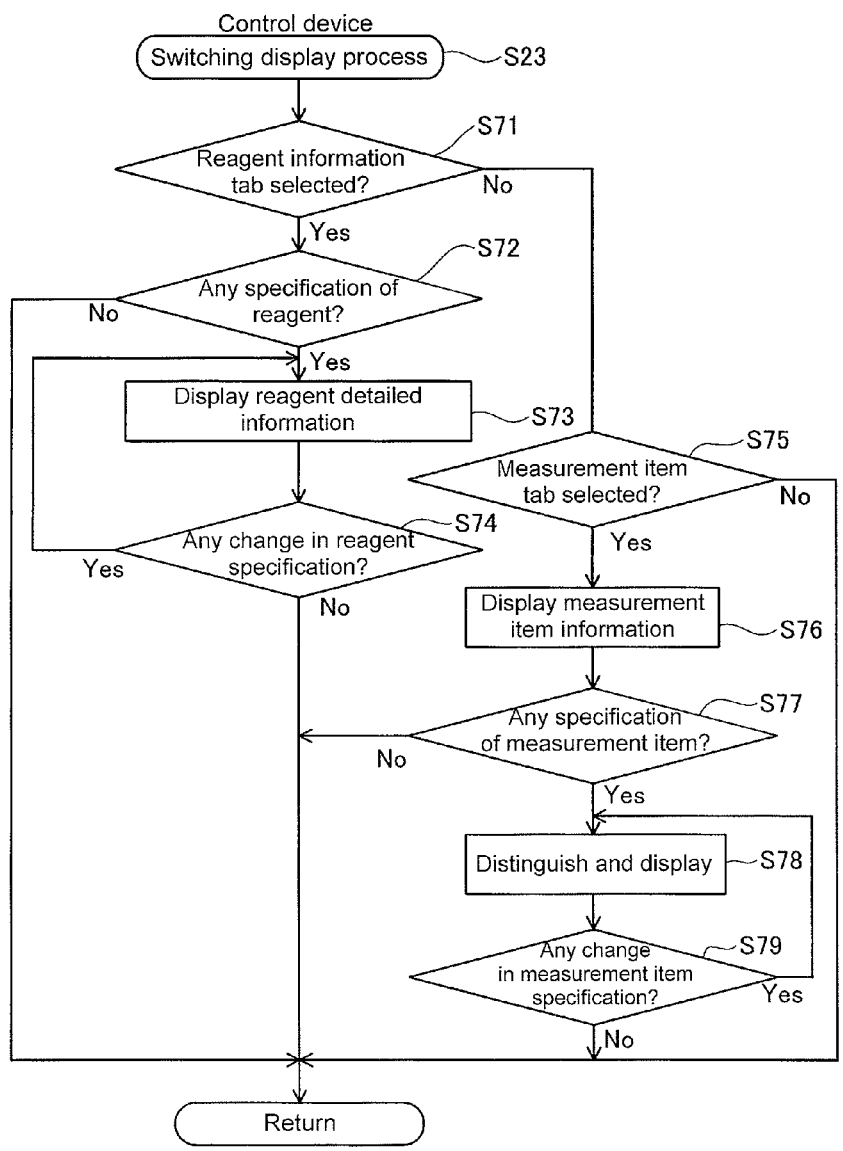
FIG. 25 is a flowchart describing a display process of the reagent management screen by the control device of the sample analyzer according to one embodiment of the present invention.

FIG. 25 is a flowchart for describing details of the switching display process in the reagent management screen of the controller 4a executed in step S23 of the flowchart shown in FIG. 19. The switching display process flow in the reagent management screen will be described with reference to FIGS. 9 to 11 and 25. The switching display process is a process of switch displaying the reagent detailed information and the measurement item information by the tab (reagent information tab 430a and measurement item tab 430b) of the reagent detailed information display area 430.

First, in step S71, whether or not the reagent information tab 430a of the reagent management screen 410 shown in FIG. 9 is selected is determined by the controller 4a. The process proceeds to step S75 if the reagent information tab 430a is not selected. Whether or not the reagent mark is specified is determined in step S72 if the reagent information tab 430a is selected. If the reagent mark is not specified, the process returns. If the reagent mark is specified, the detailed information of the reagent corresponding to the reagent mark specified in the reagent detailed information display area 430 is read out from the reagent information database 36 and displayed in step S73. Whether or not the specification of the reagent mark is changed is determined in step S74, and the display of the reagent detailed information display area 430 is changed if the specification is changed. The process returns if the specification of the reagent mark is not changed.

If the reagent information tab 430a is not selected in step S71, whether or not the measurement item tab 430b is selected is determined in step S75. If the measurement item tab 430b is not selected, the process returns. If the measurement item tab 430b is selected, the controller 4a displays the measurement item information (see FIG. 10) in the reagent detailed information display area 430 in step S76. In this case, the controller 4a displays the measurable number of times and a graph representing the measurable number of times for every measurement item with reference to the measurement item database 26. In step S77, whether or not specification of the measurement item is made is determined. If the specification of the measurement item is not made, the process returns. If the specification of the measurement item is made, in step S78, the controller 4a displays in heavy frame the reagent mark of the reagent used in the measurement of the specified measurement item so as to be displayed distinguishable from other reagent marks, as shown in FIG. 11, with reference to the measurement item database 26 of the hard disc 401d. If the measurable number of times of the measurement item to be measured is small, the reagent which remaining amount is lacking can be immediately found from a plural of reagents arranged in the reagent storing part 6 and easily replaced by specifying the measurement item. In step S79, whether or not specification of the measurement item is changed is determined, wherein the reagent mark of the specified measurement item is displayed distinguishable from other reagent marks in step S78 if the specification is changed. The process returns if the specification of the measurement item is not changed.

In a state the reagent management screen 410 is being displayed, the reagent management screen 410 is switched, as needed, according to the operation of the user by constantly performing the processes of steps S71 to S79. The switching display process in the reagent management screen 410 is performed in such manner.

Figure 26:
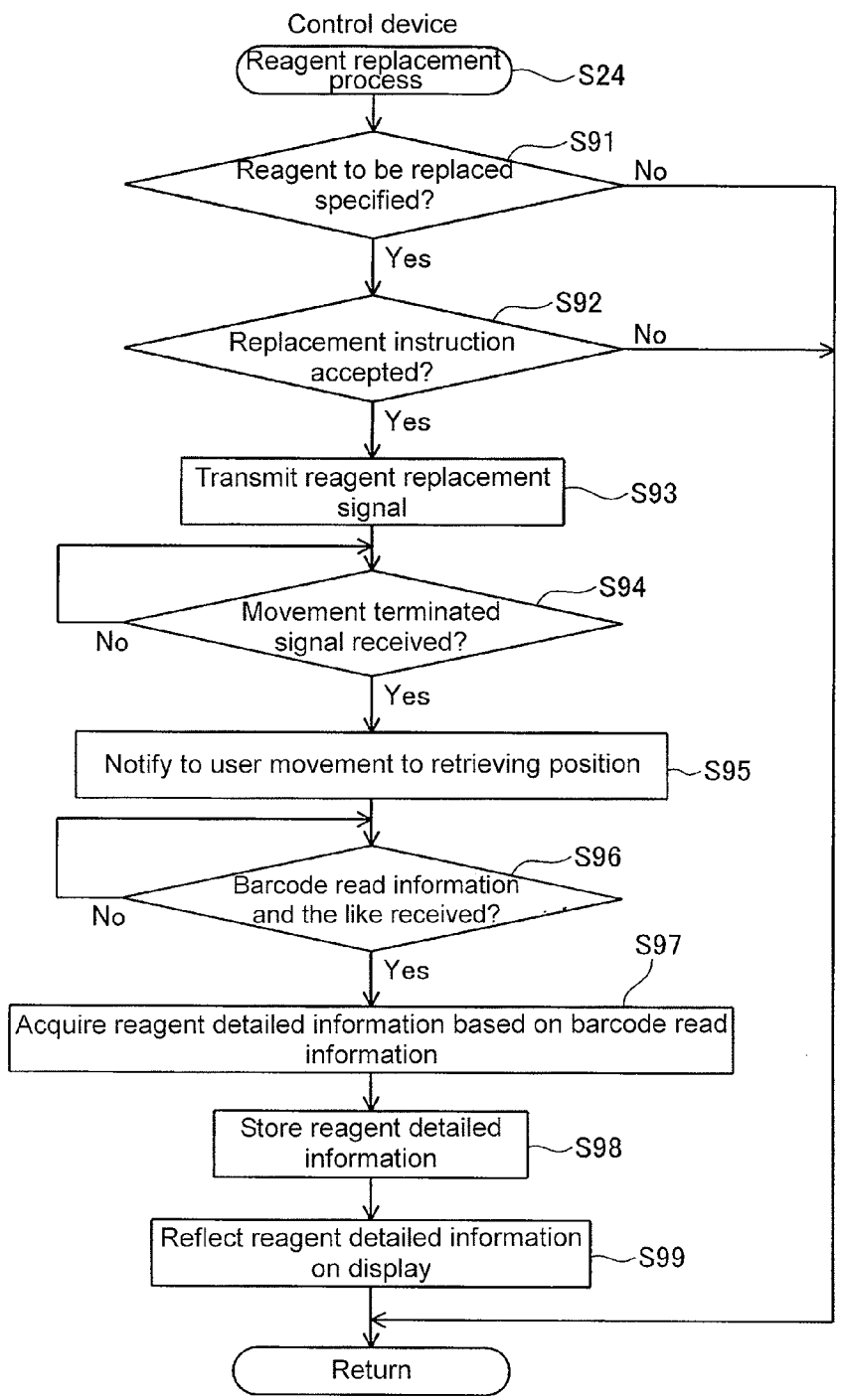
FIG. 26 is a flowchart for describing a reagent replacement process by the control device of the sample analyzer according to one embodiment of the present invention.
Figure 27:
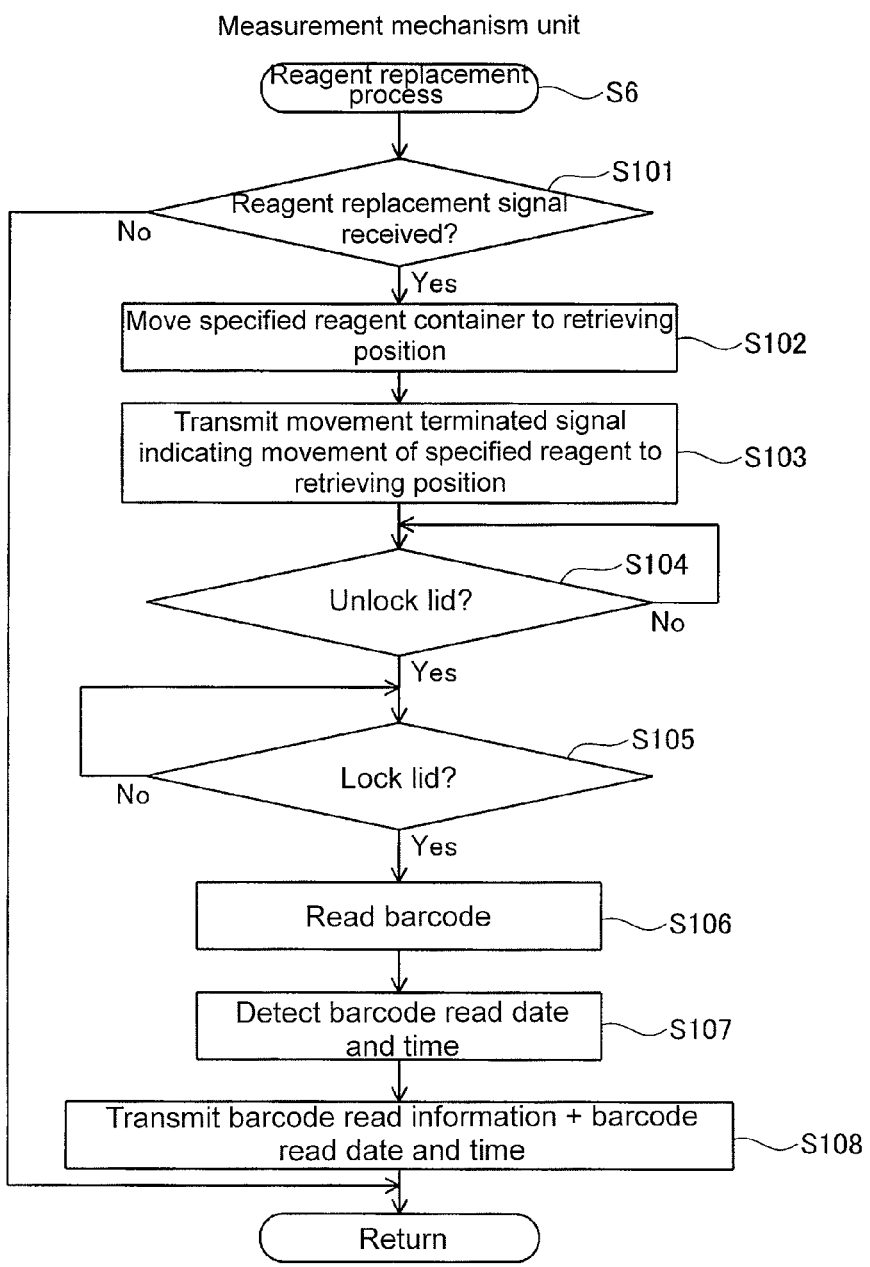
FIG. 27 is a flowchart for describing the reagent replacement process by the measurement mechanism unit of the sample analyzer according to one embodiment of the present invention.

FIG. 26 is a flowchart for describing the details of the reagent replacement process of the control device executed in step S24 of the flowchart shown in FIG. 19. FIG. 27 is a flowchart for describing the details of the reagent replacement process of the measurement mechanism unit executed in step S7 of the flowchart shown in FIG. 19. The reagent replacement process flow of the control device 4 and the measurement mechanism unit 2 of the sample analyzer 1 according to the present embodiment will be described below with reference to FIGS. 3, 9, 26, and 27.

As shown in FIG. 26, whether or not the reagent to be replaced is specified is first determined by the controller 4a of the control device 4 in step S91. If the reagent is not specified, the process is returned. If the reagent is specified, whether or not the replacement instruction is accepted is determined by determining whether or not the replacement/addition instructing button 440a is pushed in step S92. If the instruction to replace the reagent is accepted, the process proceeds to step S93. If the instruction to replace the reagent is not accepted, the process is returned. In step S93, the controller 4a of the control device 4 transmits the reagent replacement signal to the controller 501 of the measurement mechanism unit 2.

The controller 501 of the measurement mechanism unit 2 determines whether or not the reagent replacement signal is received in step S101 of FIG. 27. If the reagent replacement signal is not received, the reagent replacement process of the measurement mechanism unit 2 is terminated.

If the reagent replacement signal is received, the first driving part 502 or the second driving part 503 is controlled by the controller 501 to rotate the reagent table of the reagent replacement target so that the first reagent container rack 310 or the second reagent container rack 320 holding the specified reagent is moved to the retrieving position (lower side of first lid 30 or second lid 40) in step S102. In this process, the controller 501 issues a command to instruct the movement with respect to the drive circuit of the reagent replacement target table. When the drive circuit accepts such command, the reagent replacement flag of the status register incorporated in the drive circuit is set. That is, the reagent replacement status is set to ON with respect to the reagent replacement target table including the reagent replacement instructed by the user. Either one of the reagent replacement status of the first reagent table 11 or the reagent replacement status of the second reagent table 12 is set to ON. When the reagent container rack holding the specified reagent is moved to the retrieving position, the movement terminated signal indicating that the reagent container rack holding the specified reagent is moved to the retrieving position is transmitted to the controller 4a of the control device 4 by the controller 501 in step S103. The controller 501 can determine the rotation movement amount of each reagent table 11, 12 from the origin position of the first reagent table 11 and the second reagent table 12 by counting the number of pulses of the drive pulse signal provided to the first driving part 502 or the second driving part 503. Thus, the controller 501 can recognize that the first reagent table 11 or the second reagent table 12 has moved to the retrieving position by the movement amount from the origin position, and can generate the movement terminated signal based on such recognition.

When the movement terminated signal is transmitted from the controller 501 to the controller 4a, whether or not the movement terminated signal is received is determined by the controller 4a in step S94 shown in FIG. 26. If determined that the movement terminated signal is received in step S94, the user is notified that the reagent container rack holding the specified reagent has been moved to the retrieving position in step S95. Specifically, the rack mark displayed in a predetermined color (e.g., yellow) is displayed in a different color (e.g., green) in the reagent management screen 410. In the reagent replacing part 7, when the reagent container rack holding the specified reagent is moved to the retrieving position, the LED indicator 51 or the LED indicator 52 that emits light in red during the movement of the reagent container rack emits light in blue. The user is thereby notified that the reagent container rack holding the specified reagent has been moved to the retrieving position.

For the replacement task of the reagent, the lock mechanism of the lid (first lid 30 or second lid 40) of the table of the reagent replacement target (first reagent table 11 or second reagent table 12) is released by the user. An unlock signal is transmitted to the controller 501 from a lock detector of the lid, and whether or not the lock of the lid is released is determined by the controller 501 in step S104. In the reagent replacement task by the user, the first lid 30 or the second lid 40, which lock state is released, is detached by the user, and thereafter, the grip (grip 313 or 327) of the reagent container rack at the retrieving position (lower side of first lid 30 or second lid 40) is gripped and taken out by the user. The reagent container 300 accommodating the specified reagent is then replaced with the reagent container 300 accommodating the new reagent by the user. Thereafter, the reagent container rack arranged with the reagent after the replacement is returned to the retrieving position, and the first lid 30 or the second lid 40 is attached and locked by the user. The lock signal is transmitted to the controller 501 from the lock detector of the lid, and whether or not the lid is locked is determined by the controller 501 in step S105.

If determined that the first lid 30 or the second lid 40 is locked by the controller 501 in step S105, the barcode reading operation is performed in step S106. In the barcode reading operation, the controller 501 controls the first reagent table 11 or the second reagent table 12 and the reagent barcode reader 350 so that the reagent barcode reader 350 reads the barcode with respect to the first reagent container rack 310 or the second reagent container rack 320 arranged with the replaced reagent. Specifically, when reading the barcodes 300a, 321b to 326b or 321c to 326c of the second reagent container rack 320 and the reagent container 300 held in the second reagent container rack 320, the barcode 321b for identifying the positional information (holder number) is first read while rotating the second reagent table 12 in the direction of the arrow G (counterclockwise direction) of FIG. 5. Subsequently, the barcode 300a for identifying the detailed identification information or the barcode 321c for identifying the no-container information is read, and then the barcode 322b representing the positional information is read. The positional information (holder number) (barcodes 321b to 326b) and the detailed identification information (barcode 300a) or the no-container information (barcodes 321c to 326c) corresponding to the positional information are alternately read. The detailed identification information includes the container kind information, the reagent ID, and the lot number.

When reading the barcodes 300a, 311b to 312b, or 311c to 312c of the first reagent container rack 310 and the reagent container 300 held in the first reagent container rack 310, the second reagent table 12 is first rotatably moved so that the gap 12a (see FIG. 5) of the second reagent table 12 reaches the position facing the reagent barcode reader 350. Thereafter, similar to the case of reading the barcode 300a of the second reagent container rack 320 and the reagent container 300 held in the second reagent container rack 320, the reagent barcode reader 350 alternately reads the positional information (holder number) (barcodes 311b to 312b) and the detailed identification information (barcode 300a) or the no-container information (barcodes 311c to 312c) corresponding to the positional information through the gap 12a (see FIG. 5) while rotating the first reagent table 11 in the direction of the arrow G (counterclockwise direction). The read positional information and the detailed identification information or the no-container information corresponding to the positional information (holder number) are transmitted to the controller 501 and stored in the RAM 501c. The barcode read date and time are detected in step S106.

In step S108, the barcode read information and the barcode read date and time stored in the RAM 501c are transmitted to the controller 4a by the controller 501.

When the barcode read information and the barcode read date and time are transmitted from the controller 501 to the controller 4a, whether or not the barcode read information and the barcode read date and time are received is determined by the controller 4a in step S96 shown in FIG. 26. If determined that the barcode read information and the barcode read date and time are received in step S96, the reagent detailed information including the set date and the set time of the reagent is acquired based on the barcode read information and the barcode read date and time in step S97. Specifically, the detailed information such as the reagent name, the kind of container, the lot number, and the expiration date are acquired for all the reagents in the reagent rack holding the replaced reagent with reference to the reagent master, the reagent lot master, and the container master based on the barcode read information ((positional information), the holder number, the reagent ID, the container kind information, and the like). More specifically, the "holder number" is specified from the positional information of the barcode of the reagent container rack. The reagent ID and the reagent setting information are matched, and the "reagent name" and the "presence of stirring" are specified. Furthermore, the reagent lot number and the reagent lot setting information are matched, and the "reagent lot number" and the "expiration date" are specified. The container ID and the container setting information are matched, and the "container kind" is specified. Since the remaining amount of the reagent is calculated as described above for the reagent used in the measurement, the "usable amount" and the "remaining number of tests" are specified from the calculated remaining amount of the reagent. If the reagent is not used for the measurement not even once after the replacement, the "usable amount" and the "remaining number of tests" are not calculated. The "set date" and the "set time" for the replaced reagent are specified by the date and time where the barcode is read, and the "set date" and the "set time" for the non-replaced reagent are not specified.

In step S98, the reagent detailed information including the set date and the set time of the reagent are stored in the reagent information database 36 of the hard disc 401d. In this case, the reagent detailed information of the reagent retrieved from the reagent storing part 6 by replacement is deleted from the reagent information database 36, and the reagent detailed information of the reagent newly set in the reagent storing part 6 by replacement is newly stored in the reagent information database 36. The reagent detailed information on the non-replaced reagent is remained saved in the reagent information database 36. Since the "usable amount" and the "remaining number of tests" of the replaced reagent are unknown, "-(hyphen)" is stored in the field of "usable amount" and "remaining number of tests" of the reagent information database 36 with respect to the reagent newly set in the reagent storing part 6 by replacement. In step S99, the reagent detailed information such as the positional information, the reagent name, the kind of container, the lot number, the expiration date, the usable amount, and the remaining number of tests are reflected by the controller 4a on the first reagent mark 421, the second reagent mark 422 or the no-reagent arrangement mark 427 and the reagent detailed information display area 430 of the reagent management screen 410 (see FIG. 9). In this case, since the remaining amount of the replaced reagent is unknown, the remaining amount indicator is displayed with a predetermined color (gray).

The reagent replacement process by the control device 4 and the measurement mechanism unit 2 of the sample analyzer 1 is performed in such manner.

In the present embodiment, since the measurable number of times of the measurement item measured using a plural kinds of reagents arranged in the reagent storing part 6 is displayed, the user does not need to specify the reagent mark of the reagent used for the measurement item to be measured and check the remaining number of tests of the respective reagents. Thus, how many more times the measurement item to be measured can be measured is easily grasped.

In the present embodiment, the controller 4a acquires the measurable number of times of the measurement item measured using a plural kinds of reagents arranged in the reagent storing part 6 based on the remaining number of tests stored in the reagent information database 36. Thus, the user does not need to specify the reagent mark of the reagent used for the measurement item to be measured and check the remaining number of tests, or to perform calculations for acquiring the measurable number of times. The load of the user thus can be alleviated.

In the present embodiment, the reagent mark (first reagent mark 421 and second reagent mark 422) corresponding to the reagent used for the measurement item which specification is accepted and the diluting/cleaning fluid mark 423 are displayed with heavy frame so as to be distinguishable from other reagent marks and the diluting/cleaning fluid mark 423. Thus, even is the user is not familiar with the sample analyzer 1, the user can grasp which reagent is the reagent used for the specified measurement item (measurement item to be measured) without referencing the instruction manual of the sample analyzer 1, and the reagent mark of the relevant reagent can be easily distinguished from a plural of reagent marks. Thus, when the measurable number of times of the measurement item to be measured is few, such measurement item can be specified so that the reagent that lacks in remaining amount can be rapidly found from a plural of reagents arranged in the reagent storing part 6 and the replacement can be easily performed.

In the present embodiment, the remaining amount of each reagent is displayed by an indicator that changes modes including color and pattern of the portion that becomes the background of the reagent state information (reagent name and additional information) in the reagent name displaying portion (reagent name displaying portions 421b and 422b) of the reagent mark and the fluid name displaying portion 423b of the diluting/cleaning fluid mark. Thus, the remaining amount can be displayed using the background of the reagent mark (diluting/cleaning fluid mark), and other reagent state information can be displayed overlapping the portion displaying the remaining amount, whereby the remaining amount information and other information can be displayed in a small region compared to the case of separately displaying the remaining amount information and other information. Great amount of information thus can be displayed within the limited reagent mark of the display area.

In the present invention, the user can easily grasp from the graph how many more times the measurement item to be measured can be measured by displaying a graph reflecting the measurable number of times along with the measurable number of times.

In the present embodiment, the graph of the measurement item which measurable number of times is smaller than or equal to a predetermined value is displayed so as to be distinguishable from the graph of the measurement item which measurable number of times is greater than the predetermined value. Thus, the user can easily visually recognize the measurement item which measurable number of times is few from the plural of measurement items displayed in the reagent detailed information display area 430.

In the present embodiment, the graph of the measurement item which measurable number of times is unknown is displayed so as to be distinguishable from the graph which measurable number of times is known. Thus, the user can easily recognize the measurement item which measurable number of times is unknown from the plural of measurement items displayed in the reagent detailed information display area.

In the present embodiment, the reagent detailed information of the reagent corresponding to the specified reagent mark is displayed in the reagent detailed information display area 430. Thus, the user can check the detailed information of the reagent used for the specified measurement item at the reagent detailed information display area 430.

In the present embodiment, the sample analyzer 1 is configured to be able to switch between the reagent detailed information and the measurement item information with a tab (reagent information tab 430a and measurement item tab 430b) of the reagent detailed information display area 430. Thus, the reagent detailed information and the measurement item information can be selectively displayed in a small region compared to the case of displaying the reagent detailed information and the measurement item information in separate regions of the reagent management screen 410.

In the present embodiment, the user can grasp the name of the reagent used for the specified measurement item by displaying the name of the reagent corresponding to the reagent mark in each reagent mark.

The embodiments disclosed herein should be construed as illustrative and not restrictive in all aspects. The scope of the invention is defined by the claims rather than by the description of the embodiments, and includes all modifications equivalent in meaning to the claims and within the scope of the claims.

For instance, in the above-described embodiment, an example of displaying the reagent mark of the reagent used for the measurement of the specified measurement item with a heavy frame so as to be distinguishable from other reagent marks when the measurement item is specified has been described, but the present invention is not limited thereto. For instance, only the reagent mark of the reagent used for the measurement of the specified measurement item may be displayed largely or displayed so as to be embossed, or a mark may be displayed at the reagent mark of the reagent used for the measurement of the specified measurement item. In addition, the reagent information such as the reagent name and the remaining amount of the reagent may be displayed in the reagent mark of the reagent used for the measurement of the specified measurement item, and the reagent information such as the reagent name and the remaining amount of the reagent may not be displayed in the reagent mark of the reagent not used for the measurement of the specified measurement item. Furthermore, mask display may be performed on the reagent marks other than the reagent mark of the reagent used for the measurement of the specified measurement item.

In the above-described embodiment, the remaining amount of the reagent is displayed by an indicator in each reagent mark, but information other than the remaining amount of reagent such as remaining number of tests and expiration date of the reagent may be displayed in each reagent mark.

In the above-described embodiment, an example in which the reagent detailed information and the measurement item information are displayed in the reagent detailed information display area so as to be switchable by tabs has been described, but the present invention is not limited thereto. Each of the reagent detailed information and the measurement item information may be displayed in separate regions of the reagent management screen.

In the above-described embodiment, an example of, even when the same kind of reagent is installed in plurals, displaying the measurable number of times for every measurement item based on the total of a plural of reagents of the relevant kind has been described, but the present invention is not limited thereto. As in a variant shown in FIG. 28, the measurable number of times of the measurement item may be divided and displayed for every number of lots of the reagent. In this case, the measurement item may be selectable for every number of lots. In this case, the measurable number of times of the measurement item is determined for every lot of the reagent in the following manner.

Figure 32:
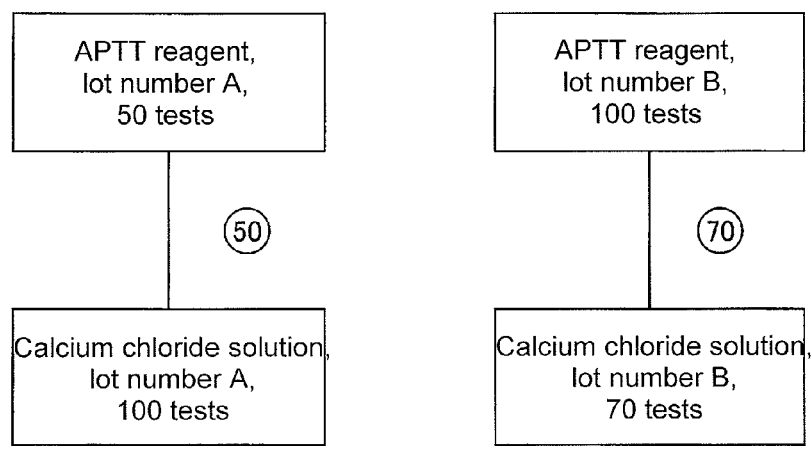
FIG. 32 is a view describing a determination method of the measurable number of times according to a variant of the present invention.

By way of example, a case of calculating the measurable number of times of the measurement item "ATTP" will be described. "APTT reagent (manufactured by Sysmex Co.)" and "Calcium chloride solution" are provided for the reagents used for the measurement item "APTT". As shown in FIG. 32, assume that the reagent storing part 6 is arranged with the APTT reagent (remaining number of tests is 50) of lot number A and the calcium chloride solution (remaining number of tests is 100) of lot number A, as well as the APTT reagent (remaining number of tests is 100) of lot number B and the calcium chloride solution (remaining number of tests is 70) of lot number B. In this case, the remaining number of tests of the APTT reagent is less for the set of lot number A, and thus the measurable number of times of the measurement item "APTT" is determined as 50. The remaining number of tests of the calcium chloride solution is less for the set of lot number B, and thus the measurable number of times of the measurement item "APTT" is determined as 70. The measurable number of times of the measurement item is determined for every number of lots in such manner.

In the embodiment described above, an example in which the display has a touch panel function and is selectable or operable by having the user directly touch the button and the like displayed on the reagent management screen has been described, but the present invention is not limited thereto. The display may be selectable or operable by specifying the button and the like displayed on the reagent management screen by a keyboard or a mouse.

In the above-described embodiment, the remaining amount of reagent in the reagent container is acquired based on the liquid level detection information obtained by the reagent dispensing arm 120 when performing the dispensing operation of the reagent, but the remaining amount of reagent may be acquired through other methods. For instance, the weight of the reagent container may be detected by a weight sensor, and the remaining amount of reagent may be acquired based on the obtained weight data. Furthermore, the remaining amount of reagent may be acquired by subtracting the amount of reagent aspirated in one dispensing operation from the predefined amount every time the dispensing operation of the reagent is performed. Moreover, the remaining amount of reagent may be acquired by detecting the liquid level of the reagent in the reagent container and determining the reagent amount in the reagent container only when the first reagent dispensing operation is performed after the startup of the apparatus, and thereafter subtracting the amount of reagent aspirated in one dispensing operation from the reagent amount determined in the first reagent dispensing operation every time the dispensing operation of the reagent is performed.

What is claimed is:
1. A sample measuring apparatus, comprising:
a reagent holder holding a plurality of reagents;
a measurement unit measuring at least one predetermined measurement item in a measurement sample, wherein the measurement sample is prepared from a sample and at least one of the plurality of reagents held by the reagent holder;
a display; and
a display controller configured to control the display to display a reagent management screen comprising:
a predetermined display area showing at least one measurable number of times indicating how many times the measuring unit is able to perform a measurement of the at least one predetermined measurement item by using the at least one of the plurality of reagents held by the reagent holder,
a second display area showing a plurality of reagent marks identifying positions of each of the plurality of reagents in the reagent holder, the second display area being separate from the predetermined display area,
a third display area displaying detailed information which includes the remaining amount information of a reagent corresponding to one of first and second reagent marks displayed in the second display area,
a measurement item specification accepting part included in the predetermined display area and configured to specify the at least one predetermined measurement item from a plurality of measurement items,
wherein, in response to said specifying the at least one predetermined measurement item in the predetermined display area, the display controller searches for reagents used for the measurement of the specified at least e predetermined measurement item and controls the second display area to change a display of the first reagent marks corresponding to found reagents to be displayed in an emphasized manner from the second reagent marks corresponding to other reagents of the plurality of reagents displayed in the second display area,
wherein each of the at least one predetermined measurement item is displayed in the predetermined display area together with the at least one measurable number of times and a graph representing the at least one measurable number of times, wherein the first and second reagent marks are specifiable, wherein the display controller controls the display so as to display, in the third display area, detailed information of a reagent corresponding to a specified reagent mark, wherein the display controller controls the display to switchably display one of the predetermined display area and the third display area via a measurement item tab and a reagent information tab.

2. The sample measuring apparatus of claim 1, further comprising:
a number obtainer for obtaining the at least one measurable number of times.

3. The sample measuring apparatus of claim 2, further comprising
a remaining amount information obtainer for obtaining remaining amount information related to remaining amounts of the reagents related to the at least one predetermined measurement item,
wherein the number obtainer obtains the at least one measurable number of times based on the remaining amount information of the reagents obtained by the remaining amount information obtainer.

4. The sample measuring apparatus of claim 3, wherein the number obtainer obtains, for the reagents related to the at least one predetermined measurement item, a remaining number of tests indicating how many times the reagent can be used for the measurement of the at least one predetermined measurement item, based on the remaining amount information of the reagents obtained by the remaining amount information obtainer, and obtains the at least one measurable number of times based on a minimum remaining number of tests among the remaining number of tests of each of the reagents related to the at least one predetermined measurement item.

5. The sample measuring apparatus of claim 1, wherein the graph is displayed so as to be distinguishable from a graph reflecting at least one measurable number of times greater than a predetermined value, when the at least one measurable number of times is smaller than or equal to the predetermined value.

6. The sample measuring apparatus of claim 1, wherein the graph is displayed so as to be distinguishable from a graph representing a definite measurable number of times, when the at least one measurable number of times is indefinite.

7. The sample measuring apparatus of claim 1, wherein the measurement unit is configured to perform measurement of another measurement item that is different from the at least one predetermined measurement item in another measurement sample prepared from the sample and another plurality of reagents held by the reagent holder; and
wherein a measurable number of times of the another measurement item is further displayed in the predetermined display area.

8. The sample measuring apparatus of claim 1, wherein the reagent management screen includes, in the predetermined display area, a first specification part specifying the at least one predetermined measurement item and a second specification part specifying the another measurement item as the measurement item specification accepting part.

9. The sample measuring apparatus of claim 1, wherein each of the first and second reagent marks comprises a remaining amount information display area for displaying remaining amount information related to a remaining amount of a reagent; and
wherein the display controller controls the display so as to display, in each remaining amount information display area, the remaining amount information of each reagent held by the reagent holder.

10. The sample measuring apparatus of claim 9, wherein the display controller controls the display so as to display the remaining amount information of each reagent held by the reagent holder by changing an appearance including at least one of color and pattern of each remaining amount information display area.

11. The sample measuring apparatus of claim 1, wherein each of the first and second reagent marks displayed in the second display area includes a reagent name display area for displaying a name of a reagent; and
wherein the display controller controls the display so as to display a name of a reagent corresponding to each reagent mark in each reagent name display area.

12. A sample measuring apparatus, comprising:
a reagent holder holding a plurality of reagents;
a measurement unit measuring at least one predetermined measurement item among a plurality of measurement items in a sample, wherein the measurement of the at least one predetermined measurement item is performed by using a plurality of reagents held by the reagent holder;
a display; and
a controller being configured to perform operations comprising:
obtaining at least one measurable number of times indicating how many times the measuring unit is able to perform a measurement of the at least one predetermined measurement item in the measurement sample prepared from the sample and the at least one of the plurality of reagents held by the reagent holder; and
controlling the display to display a reagent management screen including a predetermined display area showing the obtained at least one measurable number of times with a corresponding measurement item, a second display area showing a plurality of reagent marks identifying positions of each of the plurality of reagents in the reagent holder, the second display area being separate from the predetermined display area, and a third display area for displaying detailed information which includes the remaining amount information of a reagent corresponding to one of first and second reagent marks displayed in the second display area,
receiving a selection of the at least one predetermined measurement item shown in the predetermined display area;
in response to receiving the selection of the at least one predetermined measurement item, searching for reagents used for the measurement of the selected predetermined measurement item,
controlling the display device to change a display, in the second display area, of the first reagent marks corresponding to the found reagents to be displayed in an emphasized manner a from the second reagent marks corresponding to other reagents of the plurality of reagents displayed in the second display area, and
wherein each of the first reagent marks displays each of reagent names and each of remaining amount information related to remaining amounts of the plurality of the reagent using the measurement of the at least one predetermined measurement item,
wherein the first and second reagent marks are specifiable,
wherein the display controller controls the display so as to display, in the third display area, detailed information of a reagent corresponding to a specified reagent mark,
wherein the display controller controls the display to switchably display one of the predetermined display area and the third display area via a measurement item tab and a reagent information tab.

13. A reagent information displaying method comprising:
(a) obtaining at least one measurable number of times indicating how many times a measuring unit is able to perform a measurement of at least one predetermined measurement item in a measurement sample prepared from a sample and a plurality of reagents held by the reagent holder;
(b) displaying, on a display, a reagent management screen including a predetermined display area showing the obtained at least one measurable number of times, a second display area showing a plurality of reagent marks identifying positions of each of the plurality of reagents in the reagent holder, the second display area being separated from the predetermined display area, and a third display area for displaying detailed information which includes the remaining amount information of a reagent corresponding to one of first and second reagent marks displayed in the second display area;
(c) receiving a selection of the at least one predetermined measurement item shown in the predetermined display area and searching in a measurement item database for reagents used for the measurement of the selected predetermined measurement item; and
(d) changing a display, in the second display area, of the first reagent marks corresponding to the found reagents to be displayed in an emphasized manner from second reagent marks corresponding to other reagents of the plurality of reagents displayed in the second display area,
wherein the first and second reagent marks are specifiable,
wherein the display controller controls the display so as to display, in the third display area, detailed information of a reagent corresponding to a specified reagent mark,
wherein the display controller controls the display to switchably display one of the predetermined display area and the third display area via a measurement item tab and a reagent information tab.

14. The reagent information displaying method of claim 13, further comprising:
(e) obtaining remaining amount information related to remaining amounts of the reagents related to the at least one predetermined measurement item,
wherein the operation (a) comprises obtaining the at least one measurable number of times based on the remaining amount information of the reagents obtained in the operation (e).

15. The reagent information displaying method of claim 14, wherein the operation (a) comprises obtaining, for the reagents related to the at least one predetermined measurement item, a remaining number of tests indicating how many times the reagent can be used for the measurement of the at least one predetermined measurement item, based on the remaining amount information of the reagents obtained in the operation (e), and obtaining the at least one measurable number of times based on a minimum remaining number of tests among the remaining number of tests of the reagents related to the at least one predetermined measurement item.

16. A non-transitory storage medium which stores computer-executable programs executed by at least one processor of a sample measuring apparatus to control a display device in a sample measuring apparatus which comprises a reagent holder for holding a plurality of reagents; and a measurement unit measuring at least one measurement item in a measurement sample, prepared from a sample and reagents held by the reagent holder, comprising:
software instruction, on the computer readable medium, for enabling the computer to perform predetermined operations comprising:
obtaining at least one measurable number of times indicating how many times the measuring unit is able to perform a measurement of the at least one predetermined measurement item in the measurement sample prepared from the sample and reagents held by the reagent holder;
controlling the display device to display a reagent management screen including a predetermined display area showing the obtained at least one measurable number of times, a second display area showing a plurality of reagent marks identifying positions of each of the plurality of reagents in the reagent holder, the second display area being separate from the predetermined display area, and a third display area for displaying detailed information which includes the remaining amount information of a reagent corresponding to one of first and second reagent marks displayed in the second display area;
receiving a selection of the at least one predetermined measurement item shown in the predetermined display area;
in response to the receiving the selection, searching a measurement item database for reagents used for the measurement of the selected predetermined measurement item; and
controlling the display device to change a display, in the second display area, of the first reagent marks corresponding to the found reagents an emphasized manner from second reagent marks corresponding to other reagents of the plurality of reagents displayed in the second display area,
wherein the first and second reagent marks are specifiable,
wherein the display controller controls the display so as to display, in the third display area, detailed information of a reagent corresponding to a specified reagent mark,
wherein the display controller controls the display to switchably display one of the predetermined display area and the third display area via a measurement item tab and a reagent information tab.

17. The sample measuring apparatus of claim 1, wherein, in the second display area, the first and second reagent marks are displayed as being positioned in the reagent holder with displayed locations of the first and second marks corresponding to the positions of the plurality of reagents in the reagent holder,
wherein the location of the first and second reagent marks in the second display area remains unchanged in response to the second reagent marks being displayed in the emphasized manner, and
wherein the emphasized manner comprises the first reagent marks are changed to be displayed with a heavy frame; and
wherein the displayed first and second reagent marks are specifiable in the second display area such that the display controller controls the display so as to display, in the third display area, the detailed information of the reagent corresponding to the reagent mark specified in the second display area.

18. The sample measuring apparatus of claim 1, wherein the at least one measurement items include prothrombin time, activated partial thromboplastin time, fibrinogen content, ATIII, D dimer and FDP and wherein the emphasized manner comprises at least one of: the first reagent marks being displayed in a larger size than the second reagent marks, the first reagent marks being displayed embossed, and adding a mark to the displayed first reagent marks, the mark indicating that the first reagent marks are corresponding to the found reagents.

19. The sample measuring apparatus of claim 1, wherein the measurement sample for the at least one predetermined measurement item is prepared by using different three reagents held by the reagent holder for preparing the measurement sample.

20. The sample measuring apparatus of claim 19, wherein in response to specifying the at least one predetermined measurement item in the predetermined display area, the display controller shows the first reagent marks corresponding to the different three reagents, and each of the first reagent marks displays each of reagent names of the different three reagents.

21. The sample measuring apparatus of claim 1, wherein the second display area further displays additional information selection region comprising a plurality of items and wherein each of the items correspond to a selection to display additional information inside each of the displayed plurality of reagent marks in the second display area.

22. The sample measuring apparatus of claim 1, wherein the plurality of items comprise: a first item for selecting to display elapsed time information since a respective reagent corresponding to one of the plurality of reagent marks have been installed, a second item for selection to display measurable number of times of the measurement item that can be measured using the reagent information, a third item for selecting to display a reagent remaining amount information, and a fourth item for selecting to display no additional information.

23. The sample measuring apparatus of claim 1, wherein the display controller is configured to determine said at least one measurable number of times for the at least one predetermined measurement item as follows:
searching in a database a specification of a respective measurement item to identify reagents of the plurality of reagents used to perform a measurement of the respective measurement item,
for each of the found reagents, determining remaining amount by using the following equations:

$H = H1 - P*M,$ where H is a height of a reagent level in a container, H1 is a height of an initial position, P is number of pulses detected by a detector, and M is movement distance of one pulse detected by the detector, and $T = H*S,$ where T is the remaining amount of the reagent and S is an inner surface of the container detected by the detector
setting the one measurable number of times to equal to the remaining amount of a reagent from the found reagents with a lowest remaining amount,
wherein, in response to detecting that the reagent occupies a plurality of containers, adding the remaining amount in each of the plurality of containers to determining the remaining amount of the reagent, and
wherein, in response to not being able to detect the remaining amount in one of the plurality of containers, skipping the container in said adding operation.

* * * * *